(12) United States Patent
Cummings et al.

(10) Patent No.: US 11,911,191 B2
(45) Date of Patent: Feb. 27, 2024

(54) MEDICAL DEVICE TRANSPORTATION SYSTEMS

(71) Applicant: Boston Scientific Scimed, Inc., Maple Grove, MN (US)

(72) Inventors: Nathan T. Cummings, Worcester, MA (US); Jenny Dandin, Worcester, MA (US); Michele E. Dalena, Boston, MA (US); Alyson Borzillo, Boston, MA (US); Ryan LaFlamme, Ham Lake, MN (US); Joshua Talsky, Brooklyn, NY (US); Mark Collins, Cedarburg, WI (US); John LaRoi, Libertyville, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/123,765

(22) Filed: Dec. 16, 2020

(65) Prior Publication Data

US 2021/0186641 A1 Jun. 24, 2021

Related U.S. Application Data

(60) Provisional application No. 62/953,358, filed on Dec. 24, 2019.

(51) Int. Cl.
*A61B 50/36* (2016.01)
*A61B 50/00* (2016.01)
*A61B 50/30* (2016.01)

(52) U.S. Cl.
CPC ........ *A61B 50/36* (2016.02); *A61B 2050/005* (2016.02); *A61B 2050/3011* (2016.02); *A61B 2050/314* (2016.02)

(58) Field of Classification Search
CPC .............. A61B 50/36; A61B 2050/005; A61B 2050/314; A61B 2050/3011; B65D 1/34
(Continued)

(56) References Cited

U.S. PATENT DOCUMENTS 3,770,119 A 11/1973 Hultberg et al.
4,871,046 A * 10/1989 Turner ..................... A61B 7/02
D24/134

(Continued)

FOREIGN PATENT DOCUMENTS

DE 202009014228 U1 3/2010
DE 202016105248 U1 12/2016
(Continued)

OTHER PUBLICATIONS

"ETS PLUS Secure Endoscope Transportation with Hygienic Focus", Olympus brochure EO428343EN (2017) 3 pages.
(Continued)

*Primary Examiner* — Steven A. Reynolds
(74) *Attorney, Agent, or Firm* — Seager, Tufte & Wickhem, LLP

(57) ABSTRACT

A system for containing and transporting a medical device may include a container including a bottom face and surrounding side faces as a closed first end and an open second end to form an inner portion for receiving and retaining the medical device. At least a portion of one or more of the side faces may have an indentation extending along a length of the respective side face. A liner and cover may be removably enclosable about the container. The liner may be extendable over the side faces to line the inner portion of the container. The cover may enclose the medical device in the container between the liner and cover. The indentation may be formed
(Continued)

into the inner portion of the container. The container may be compatibly receivable in a first transportation device in a first orientation.

16 Claims, 22 Drawing Sheets

(58) Field of Classification Search
USPC .................................................. 206/363, 557
See application file for complete search history.

(56) References Cited

U.S. PATENT DOCUMENTS

| | | | |
|---|---|---|---|
| 5,732,821 | A | 3/1998 | Stone et al. |
| 5,868,189 | A * | 2/1999 | Jarvis ...................... B63H 7/02 150/165 |
| 6,641,781 | B2 | 11/2003 | Walta |
| 6,749,063 | B2 * | 6/2004 | Parker ..................... A61B 50/30 206/363 |
| 7,744,832 | B2 | 6/2010 | Horacek et al. |
| 8,042,688 | B2 | 10/2011 | Parks et al. |
| 8,561,820 | B2 | 10/2013 | Kitt et al. |
| 8,733,551 | B2 | 5/2014 | Parker et al. |
| 8,747,739 | B2 | 6/2014 | Parker et al. |
| 8,789,695 | B2 | 7/2014 | Mason |
| 8,807,354 | B2 | 8/2014 | Kitt et al. |
| 8,905,258 | B2 * | 12/2014 | Javid ..................... A47J 36/06 229/87.08 |
| 8,939,287 | B2 | 1/2015 | Markovitch |
| 9,265,578 | B2 | 2/2016 | Pacey |
| 9,788,913 | B2 * | 10/2017 | Ghosh .................... A61B 46/00 |
| D818,841 | S | 5/2018 | Newton |
| D819,404 | S | 6/2018 | Metaxatos et al. |
| D819,409 | S | 6/2018 | Newton |
| 10,086,131 | B2 | 10/2018 | Okihara |
| 10,405,938 | B2 | 9/2019 | Ramsey |
| D891,777 | S | 8/2020 | Newton |
| 2003/0056698 | A1 * | 3/2003 | Comeaux ............... A61B 50/13 108/90 |
| 2006/0272979 | A1 * | 12/2006 | Lubbers ................. A61B 17/02 206/557 |
| 2006/0273084 | A1 * | 12/2006 | Baker .................... B65D 51/00 220/23.4 |
| 2007/0215507 | A1 * | 9/2007 | Glenn .................... A61B 50/33 206/557 |
| 2010/0158753 | A1 | 6/2010 | Friderich et al. |
| 2011/0192744 | A1 * | 8/2011 | Parker .................... A61B 50/30 206/363 |
| 2012/0152289 | A1 | 6/2012 | Smith et al. |
| 2014/0138269 | A1 * | 5/2014 | Ghosh .................... A61B 90/30 206/370 |
| 2015/0144515 | A1 | 5/2015 | Chartres et al. |
| 2015/0257632 | A1 * | 9/2015 | Ramsey ................. A61B 90/92 206/204 |
| 2015/0259122 | A1 | 9/2015 | Parker |
| 2016/0058518 | A1 | 3/2016 | Mason |
| 2017/0056122 | A1 | 3/2017 | Ramsey |
| 2018/0110580 | A1 | 4/2018 | Hynes |
| 2018/0134453 | A1 | 5/2018 | Wassenburg |
| 2019/0167824 | A1 | 6/2019 | Rhodes et al. |
| 2020/0205925 | A1 | 7/2020 | Cummings et al. |
| 2021/0186641 | A1 | 6/2021 | Cummings et al. |

FOREIGN PATENT DOCUMENTS

| | | |
|---|---|---|
| DE | 102017008894 A1 | 3/2018 |
| EP | 2501321 A2 | 9/2012 |
| EP | 3136941 A2 | 3/2017 |
| EP | 3288437 A1 | 3/2018 |
| GB | 2525694 A | 11/2015 |
| WO | 03034936 A1 | 5/2003 |
| WO | 2015166240 A2 | 11/2015 |
| WO | 2017075001 A1 | 5/2017 |
| WO | 2020139891 A1 | 7/2020 |

OTHER PUBLICATIONS

"MEDIVATORS™ CLEANASCOPE™ Transport & Short Term Storage System", MEDIVATORS—A Cantel Medical Company brochure (2015) 4 pages.
"SafeCAP® Endoscope Transport and Short-Term Storage System", ClinicalChoice brochure (2019) 2 pages.
International Search Report and Written Opinion, Application No. PCT/US2019/068487, dated Apr. 22, 2020, 11 pages.
International Search Report and Written Opinion dated Mar. 23, 2021 for International Application No. PCT/US2020/065284.

* cited by examiner

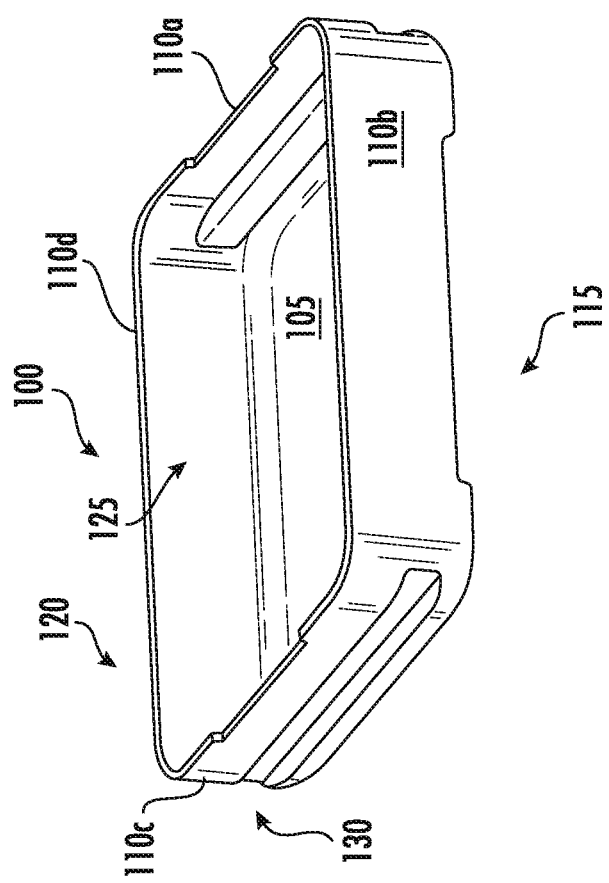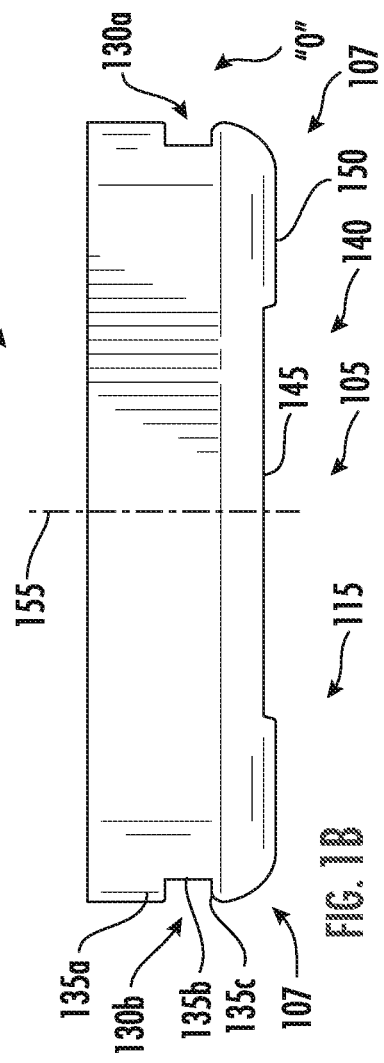

SECTION E-E

SECTION H-H

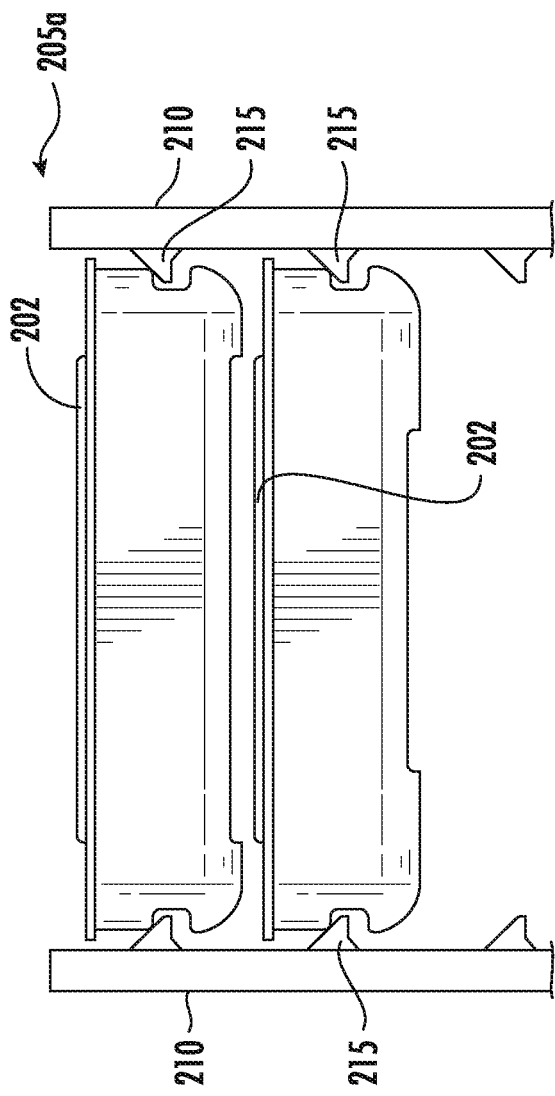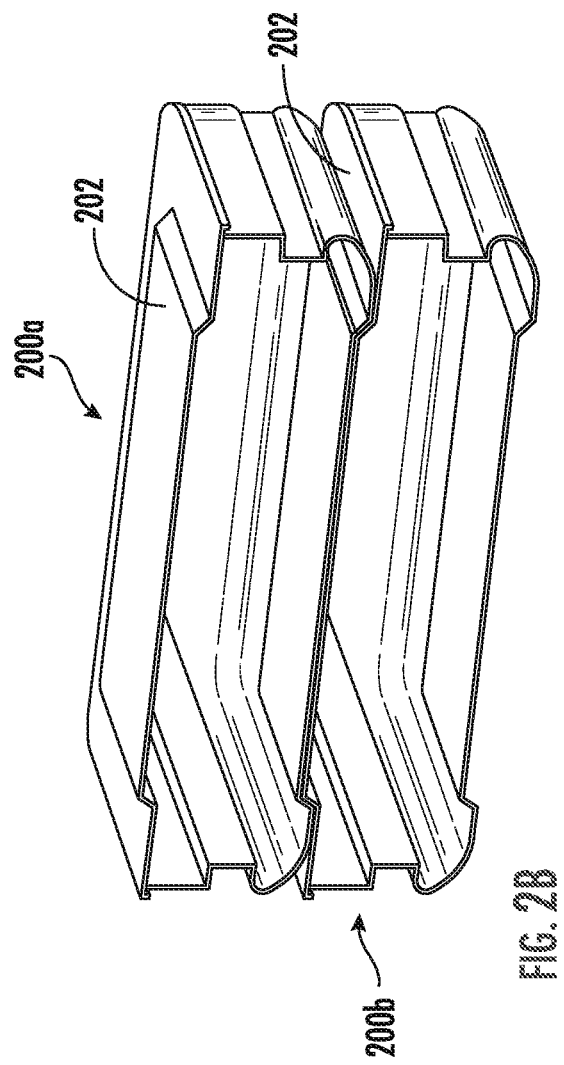

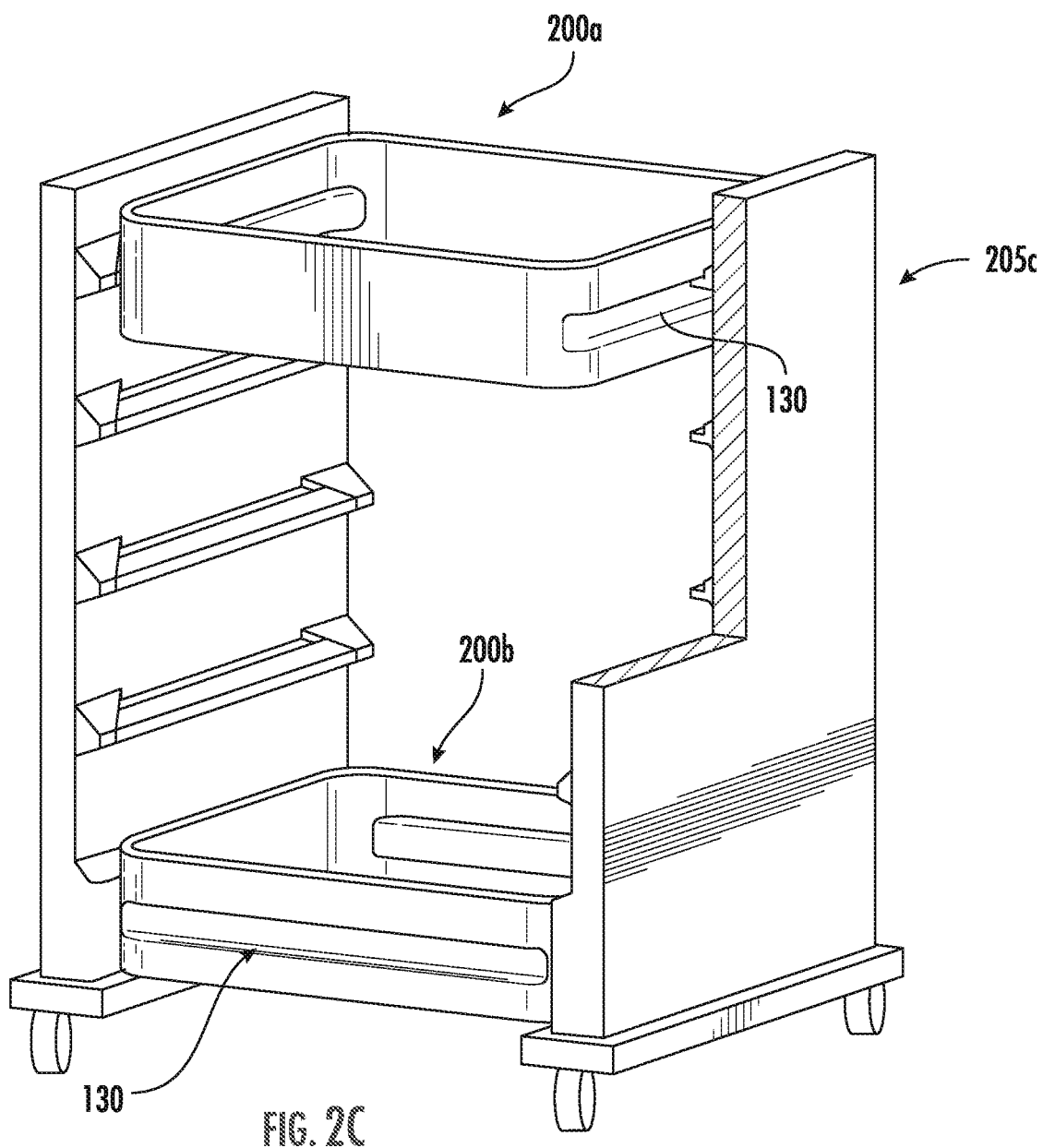

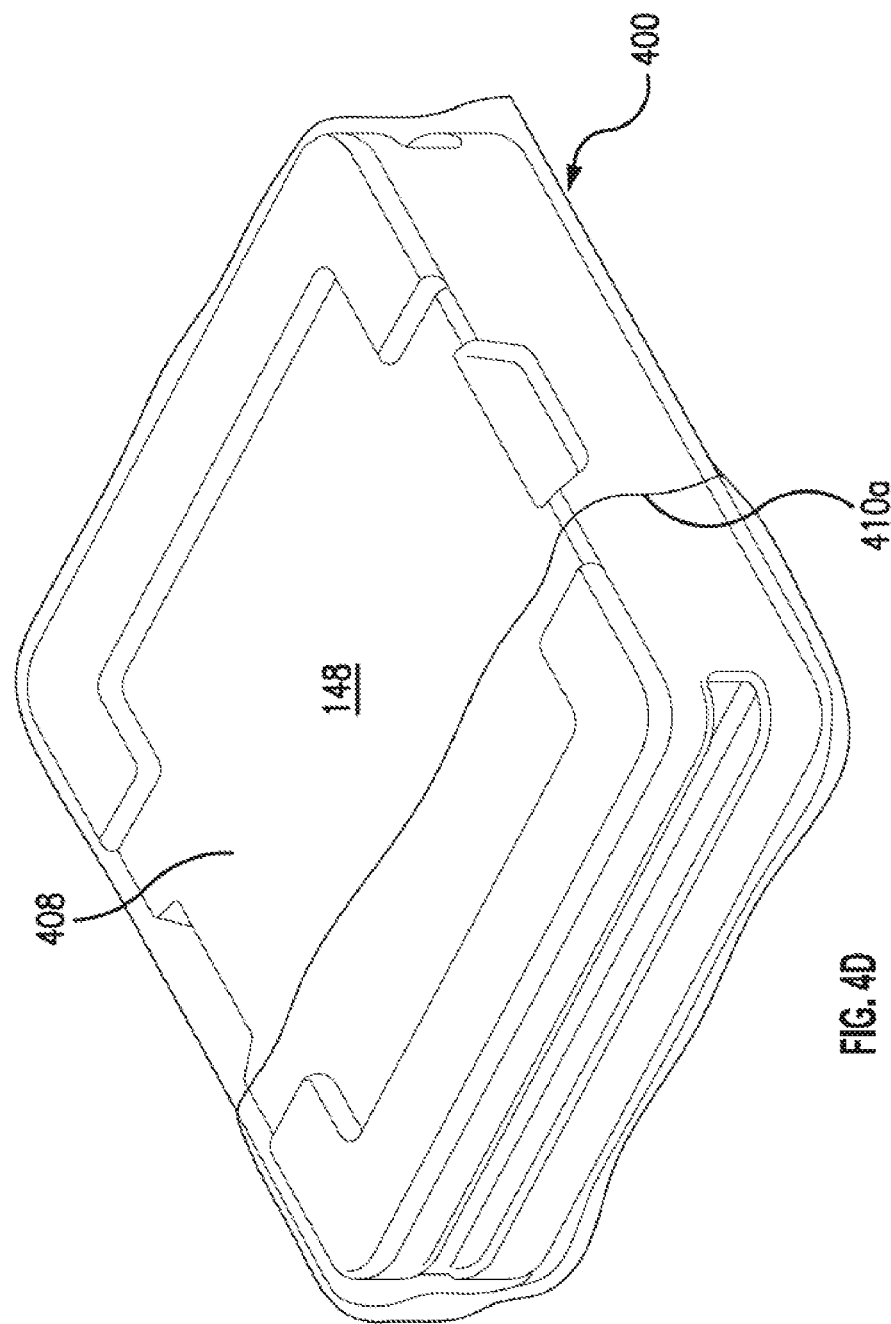

MEDICAL DEVICE TRANSPORTATION SYSTEMS

PRIORITY

This application claims the benefit of priority under 35 USC § 119 to U.S. Provisional Patent Application Ser. No. 62/953,358, filed Dec. 24, 2019, which is incorporated by reference herein in its entirety and for all purposes.

FIELD

The present disclosure relates generally to containment and transportation systems, and more particularly, containers and methods for transporting medical devices.

BACKGROUND

Some devices, including endoscopes, may be reusable for on-going patient use. Medical facilities, such as clinics or hospitals, may manually clean and high-level disinfect each device between use, and may need to transport the devices from a reprocessing or storage location to another location for use in a medical procedure. Clean medical devices may be deliverable to the medical professional for performing a medical procedure and used medical devices may be deliverable to the reprocessing or storage location.

One challenge for medical facilities is to maintain a workflow of the clean and used medical devices to minimize cross-contamination and a potential spread of infections and/or diseases. Current medical device containment and transportation systems used in medical facilities may be difficult to clean, e.g., including configurations that may allow for bacteria and other contaminants to remain on the surfaces even after disinfecting processes. Clean medical devices may be at risk of contamination in the event the containment systems are not thoroughly disinfected.

Additionally, existing containment and transportation systems may only be used exclusively together, so that medical facilities may be limited to a particular container to be used with a transportation system. Thus, medical facilities may be unable to swap out particular container configurations in different types of transportation systems as desired.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a system for containing and transporting a medical device may include a container including a bottom face and surrounding side faces as a closed first end and an open second end to form an inner portion for receiving and retaining the medical device. At least a portion of one or more of the side faces may have an indentation extending along a length of the respective side face. A liner may be removably enclosable about the container. The liner may be extendable over the side faces to line the inner portion of the container. The liner may be conformable to a profile of the container. The indentation may be formed into the inner portion of the container such that the container is compatibly receivable in a first transportation device in a first orientation.

In various of the foregoing and other embodiments of the present disclosure, the bottom face of the container may include a contour, such that the container may be compatibly receivable in the first transportation device in a second orientation different from the first orientation. A first cover may be removably enclosable about the container and extendable over at least a portion of the side faces and across the open second end of the container to enclose the inner portion. A second cover may be removably enclosable about the container and extendable over at least a portion of the side faces and across the open second end of the container to enclose the inner portion. The first cover may be exchangeable with the second cover for visual verification of a condition of the medical device. The first cover may be reversible, as opposed to a second cover, with each side of the reversible cover for visual verification of a different condition of the medical device. The container may be compatibly receivable in a second transportation device. The second transportation device may be different from the first transportation device, such that the container may be exchangeable between the first transportation device and the second transportation device. The liner, first cover, and/or second cover may be removably enclosable about the container in a "pillow sham"-type or "sandwich bag"-type configuration. One or more handles may be formed in a container as indentations in the side face, bottom face, or the corner between a side face and the bottom face, or some combination thereof. The handles may be formed with a width, depth and height sized to accommodate a user's fingers when grasping the container. The side faces of a container may extend along a straight line from the open second end to the closed first end vertical to the bottom face, or the side faces may extend along a straight line that tapers inward from vertical from the open second end to the closed first end, or some side faces may be vertical while others may be tapered inward. The indentations formed into the inner portion of a container may have a uniform height of opening along the length of the indentation, or the opening may increase in height toward one or both ends of the indentation, such that the container may be further compatibly receivable in a transportation device. The contour of the bottom face of the container may include an indentation that may extend from the bottom face into the inner portion of the container.

According to an exemplary embodiment of the present disclosure, a container for containing and transporting a medical device may include a bottom face and surrounding side faces as a closed first end and an open second end to form an inner portion for receiving and retaining the medical device. At least a portion of one or more of the side faces may have a first indentation extending along a length of the respective side face. The first indentation on the at least a portion of the one or more side faces may be formed into the inner portion of the container. The container may be compatible to be receivable in a first transportation device.

In various of the foregoing and other embodiments of the present disclosure, a protrusion may extend from at least a portion of one or more of the side faces and may be positionable relative to the first indentation on at least the portion of the one or more of the side faces of the container. The portion of one or more of the side faces of the container may include a second indentation. A liner may be removably enclosable about the container. The liner may be extendable over the side faces to line the inner portion of the container, such that the liner may be conformable to a profile of the container. A first cover may be removably enclosable about the container and extendable over at least a portion of the side faces and across the open second end of the container to enclose the inner portion. A second cover may be removably enclosable about the container and extendable over at least a portion of the side faces and across the open second end of the container to enclose the inner portion. The first cover may be exchangeable with the second cover for visual verification of a condition of the medical device. The first cover may be reversible, as opposed to a second cover, with each side of the reversible cover for visual verification of a different condition of the medical device. The liner, first cover, and/or second cover may be removably enclosable about the container in a "pillow sham"-type or "sandwich bag"-type configuration. The container may be compatibly receivable in a second transportation device. The second transportation device may be different from the first transportation device, such that the container may be exchangeable between the first transportation device and the second transportation device. A closure feature of the liner may be cross-wise with a closure feature of the first or second cover. A closure feature of the liner may be parallel and staggered with a closure feature of the first or second cover. First and second edges of the closure feature of the liner may at least partially overlap each other. First and second edges of the closure feature of the liner may at least partially abut each other. First and second edges of the closure feature of the first or second covers may at least partially overlap each other. First and second edges of the closure feature of the first or second covers may at least partially abut each other.

According to an exemplary embodiment of the present disclosure, a method for containing and transporting a medical device may include enclosing a liner about a container. The container may include a bottom face and surrounding side faces as a closed first end and an open second end to form an inner portion. At least a portion of one or more of the side faces may have an indentation extending along a length of the respective side face. The liner may be extendable over the side faces and the inner portion of the container, such that the liner may be conformable to a profile of the container. A medical device may be received in the inner portion of the container. A first cover may be enclosed about the container. The first cover may extend over at least a portion of the side faces and across the open second end of the container to enclose the inner portion. The first cover may be exchangeable with a second cover for visual verification of a condition of the medical device. The first cover may be reversible, as opposed to a second cover, with each side of the reversible cover for visual verification of a different condition of the medical device. The liner, first cover, and/or second cover may be removably enclosable about the container in a "pillow sham"-type or "sandwich bag"-type configuration. The indentation may be formed into the inner portion of the container such that the container may be compatibly receivable in a first transportation device in a first orientation. The bottom face of the container may include a contour, such that the container may be compatibly receivable in the first transportation device in a second orientation different from the first orientation. The container may be compatibly receivable in a second transportation device. The second transportation device may be different from the first transportation device, such that the container may be exchangeable between the first transportation device and the second transportation device. The first cover may be exchanged with the second cover in response to a change in the condition of the medical device.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 1A-1I illustrate an exemplary embodiment of a container in accordance with the present disclosure.

FIG. 2A illustrates partial view of an exemplary embodiment of a containment and transportation system in accordance with the present disclosure;

FIG. 2B illustrates a cross-sectional view of an exemplary embodiment of a plurality of containers in a stacked configuration in accordance with the present disclosure;

FIGS. 2C-2D illustrate exemplary embodiments of a containment system in accordance with the present disclosure;

FIGS. 4A-4G illustrate exemplary embodiments of a container liner and cover in accordance with the present disclosure.

DETAILED DESCRIPTION

Figure 1C:
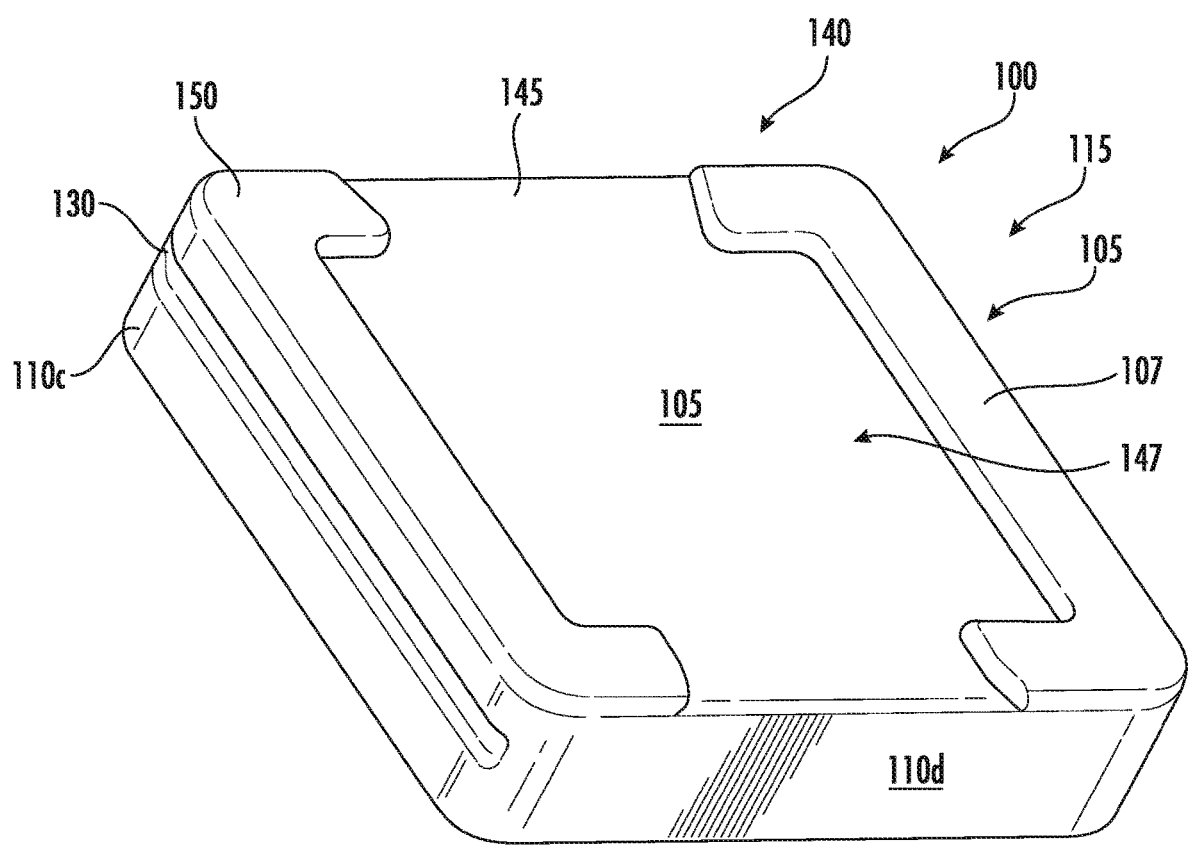

The present disclosure is not limited to the particular embodiments described herein. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Exemplary embodiments of containment and transportation systems and methods according to the present disclosure may be configured for improved cleanability or disinfection, to reduce a risk of contamination of medical devices. Exemplary embodiments may also be configured to minimize or prevent inadvertent re-use of a device that has not been reprocessed, and/or inadvertently reprocessing an already reprocessed device that is thought to have been used. As described above, existing systems may be configured with features such as undercuts, lips, notches, or the like, that may trap contaminants. During handling, a medical professional may contact the contaminated undercut or lip, potentially transferring contaminants to a clean medical device and thereby increasing a risk of spreading diseases to a patient.

A containment system in accordance with the present disclosure may include a container having an improved design to minimize contamination for receiving, handling and retaining a medical device, which may be transported throughout a medical facility for reprocessing and patient use. Referring now to FIGS. 1A-1G, an exemplary embodiment of a container 100 is depicted. The container 100 may be formed as a tray, or basket, or a shallower type of receptacle, for receiving and retaining a medical device. The container 100 may have a bottom face 105, and surrounding side faces 110a-110d, to form the container having a closed first end 115 and an open second end 120. The open-ended container 100 may have an inner portion 125 formed by the bottom face 105 and surrounding side faces 110a-110d, e.g., such that a medical device is receivable by placement on the bottom face 105 and retainable inside the container by the surrounding side faces 110a-110d. In some embodiments, the side faces 110a-110d may extend along a straight line that is vertical to the bottom face 105 (e.g., FIGS. 1A-1C), and in other embodiments one or more of side faces 110a-110d may extend along a straight line that tapers inward from the open second end 120 to the closed first end 115. For example, referring to FIGS. 1D-1I, the container 100 may include vertical sides faces 110b, 110d along the front and back of the container, while side faces 110a, 110c along the sides of the container including indentations 130 may taper slightly inward from vertical extending from the open second end 120 to the closed first end 115. FIG. 1E depicts a taper of $\theta_{SW}$ degrees from vertical that may be a range of 0 degrees to about five degrees. The taper may help to provide clearance between side surfaces 110a, 110c of the container and the sides of a transportation device when the container is loaded in the device. Alternatively, or additionally, the taper may help in the manufacturing process for the container, e.g., to aid in releasing the container from an injection mold if that forming technique is used.

In some embodiments, the container 100 may be formed as a rectangle, or square, e.g., having four side faces 110a-110d, although it is envisioned that the container may be formed with any number "n" of side faces. Additionally, the container 100 may have rounded edges 107 connecting the bottom face and surrounding side faces, which may be advantageous for a more thorough disinfection as well as handling. In embodiments with a tapered side face, the side face may be made to follow a straight line from the open second end to the closed first end and tangential to the apex of the rounded edge 107 (see FIG. 1E). The container may be formed of a substantially rigid material, such as a plastic or composite, and may be thermoformed or molded as a single piece to its configuration.

The container 100 may have one or more indentations 130. In embodiments, a first indentation 130a may extend along at least a portion of a first side face 110a, e.g., substantially parallel to the bottom face 105. Similarly, a second indentation 130a may extend along at least a portion of a third side face 110c, e.g., substantially parallel to the bottom face 105 and in alignment with the first indentation 130a. The indentations may extend along the full length of the respective face, although in some embodiments the indentations may extend along a portion of the side face. In some embodiments, the container 100 may have two indentations 130a, 130b, along opposing side faces, to be received by a transportation device. Indentations may also be included in at least a portion of the other side faces 110b, 110d, etc. The indentations 130 may be substantially symmetrical to each other, e.g., so that the container 100 may be receivable into a transportation device in an upright position. In embodiments, the container may be receivable into a cart, for transport in a medical facility.

The indentations 130 may be formed to extend inward into the inner portion 125. In some embodiments, the indentations 130 may be formed as rails, e.g., having a rectangular cross-section. The indentations may be formed inward so that a user, e.g., a medical professional, may grip the container 100 by the indentations 130 (e.g., surfaces 135a). The medical professional may alternatively and/or additionally handle the container 100 via the bottom face 105 and/or side faces 110a-110d (e.g., rounded edges 107). In embodiments, the medical professional may slide a container 100 in and out of a transportation device, such as a cart, and may carry the container 100 to a reprocessing location and/or a patient procedure location. The indentations 130 may have surfaces 135a-135c formed substantially perpendicular to each other (90 degrees±10 degrees), although in some embodiments one or more of the surfaces may form an obtuse angle (>90 degrees). The surfaces 135a-135c of the indentations 130 may be cleanable, e.g., contaminants may not be trapped in the indentations, so that when the medical professional grips and carries the container 100 as needed, cross-contamination may be minimized. In embodiments, corners of the surfaces 135a-135c may have radii to enhance cleanability of the container 100, which may be dimensioned between approximately 0.100 to 0.180 inches for cleaning. The surfaces 135a-135c may be a "C" or "U" shape, to create an opening "o". As described below, the opening "o" may be sized as desired, e.g., to allow for handling by a medical professional and/or for receiving a cover, a liner, or both, e.g., based on the surface 135b formed substantially perpendicular relative to the bottom face 105.

In some embodiments, the indentations 130 may have a uniform height of opening along the side face (e.g., FIG. 1C), and in other embodiments the indentions may have a height of opening that increases at one or both ends of the indentation. Referring to FIG. 1F, container 100 includes indentations 130 extending along the side faces 110a, 110c, with flared end openings 132. The height of the middle length of indentation 130 is represented as $d_{CI}$ and the height of the flared end openings 132 is represented as $d_{TT}$. Height $d_{TT}$, may gradually decease to height $d_{CI}$, through the length of the flare end openings 132. For example, at a maximum height, flared end openings 132 may be approximately 30%-50% greater than the height of the middle length of indentations 130. Flare end openings may assist with aligning the opening of indentation 130 with the rails 215 of a transportation device 505a, 505c, as the container is loaded into the device. Flare end openings 132 may also provide some gap clearance between the edges of the opening of indentation 130 and the edges of rails 215 to facilitate sliding the container into a transportation device along the rails. In some embodiments, one or both ends of indentations 130, whether flared or not, may include a portion 135d that wraps around from the side face with the indentation to the adjacent side face (see, e.g., FIG. 1D). This may assist with alignment and starting the indentation along the rails of a transportation device once aligned.

In embodiments, the indentations 130 may be formed to allow for the container 100 to be compatibly receivable into a plurality of transportation devices. For example, the container 100 may be receivable in a first transportation device, and a second transportation device, where the first and second transportation devices have differing configurations. It is understood that the container may be compatibly receivable in any number "n" of transportation devices of differing configurations. The indentations may extend inwardly into the inner portion 125 a depth such that the container is adaptably receivable into carts having different configurations. In some embodiments, the container 100 and the indentations 130 may be dimensioned to be receivable in the transportation devices. In this matter, the container 100 may be compatible with a variety of transportation systems (see FIGS. 2A-2D).

Additional features may also include contouring and/or beveling on the rounded edges 107 at the corners of the container 100 underneath the indentations 130, as described in more detail in U.S. patent application Ser. No. 16/726,588, filed Dec. 24, 2019, and titled "Medical Device Containment and Transportation Systems and Methods," the entirety of which application is incorporated by reference herein.

The bottom face 105 of the container 100 may include a contour 140. The contour 140 may include recessed portions 145, e.g., an outer surface 148 of the bottom face 105 may be disposed inward from portions 150 of the bottom face 105. The recessed portions 145 may be positioned substantially along the side faces 110b, 110d opposite of side faces having the indentations 130a, 130b, and/or along a central portion 147 of the bottom face 105. In some embodiments, side faces 110a, 110c may have at least the portions 150.

Figure 1D:
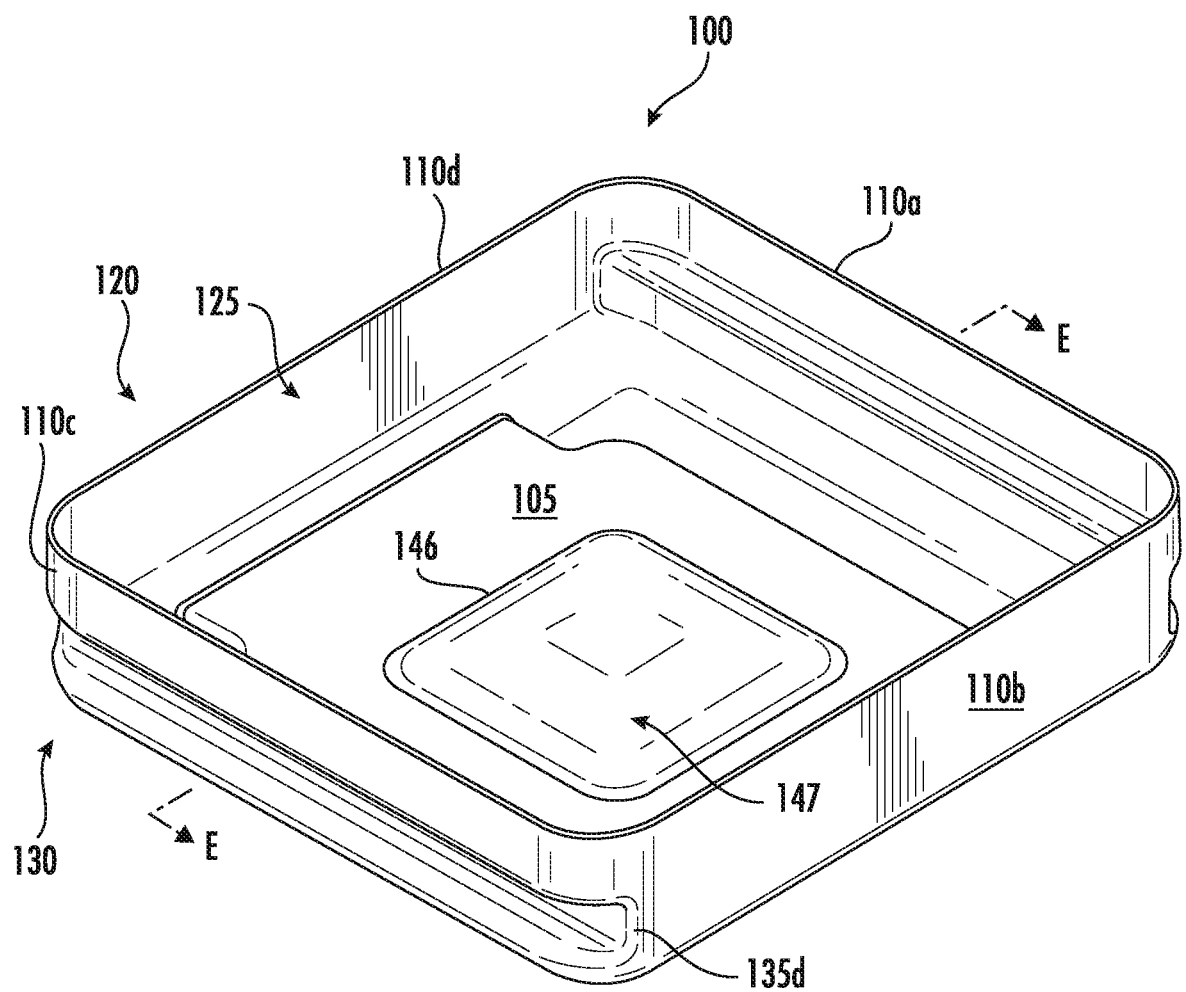
Figure 1E:
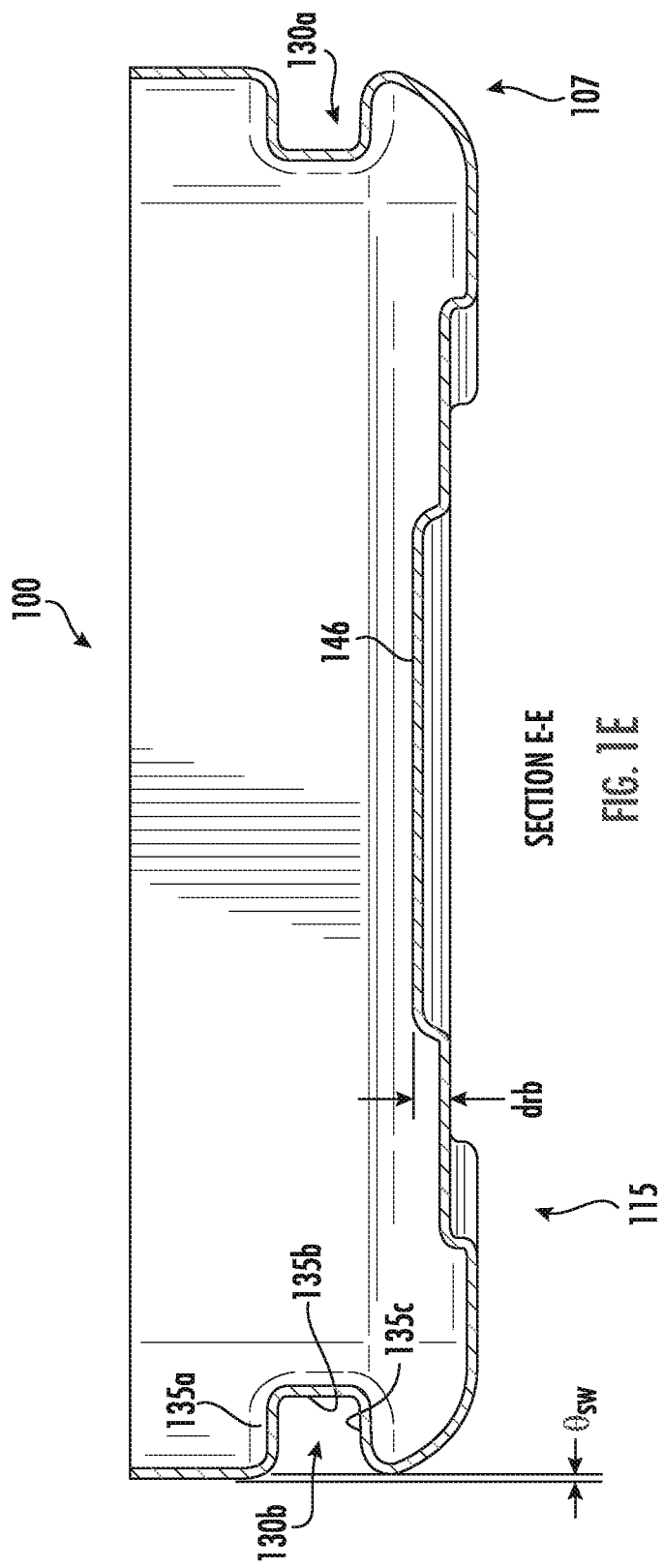
Figure 1F:
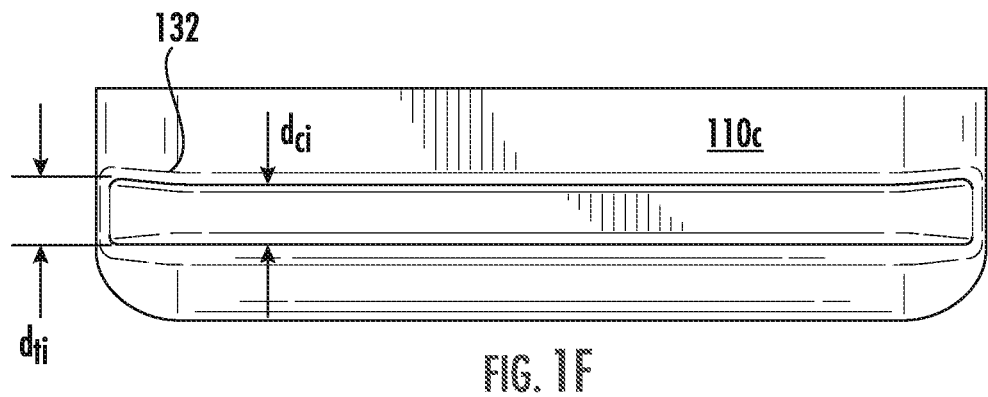
Figure 1G:
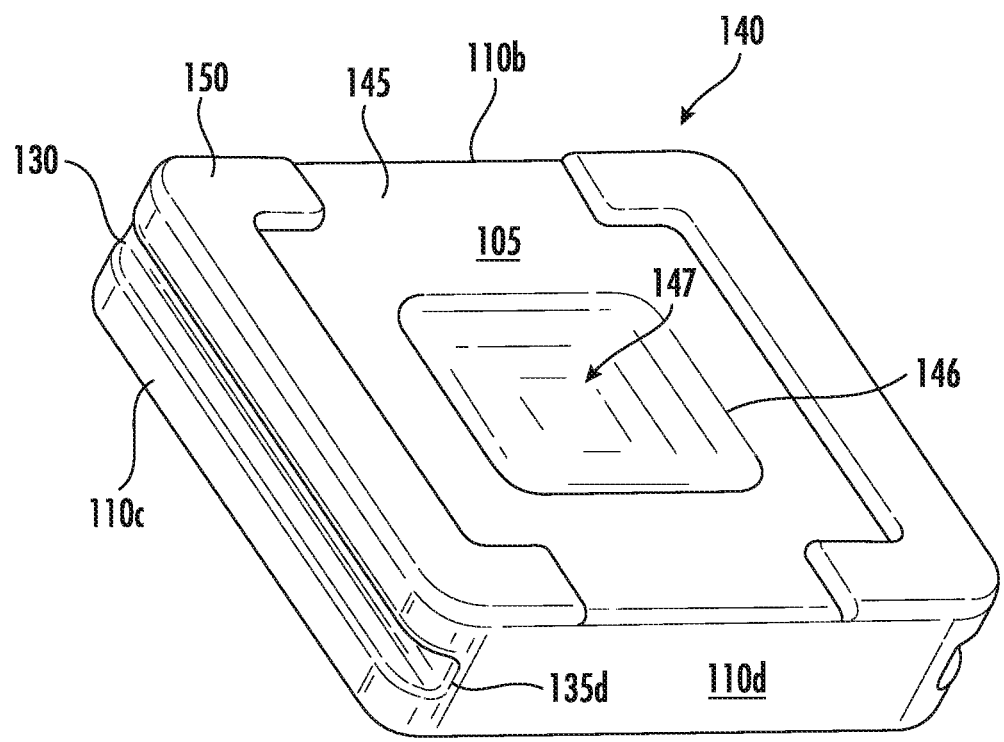

In some embodiments, the central portion 147 of the bottom face 105 may include an indentation 146 that extends from the surface of the recessed portion 145 of the bottom face 105 into the inner portion 125 (e.g., FIGS. 1D-1H). Referring to FIGS. 1D-1E, indentation 146 may have a square shape and extend into inner portion 125 a distance $d_{RB}$ that may range from about 0 mm. to about 25 mm. As shown, indentation 146 may extend into inner portion 125 a distance $d_{RB}$ of 0.4 in. (10.16 mm). The shape of indentation 146 is depicted as a square, but may be any number of other shapes, such as circular, oval, rectangular, etc. The profile of the indentation 146 may have a plateau-like cross-section, as shown, with a step-up around the edges and a relatively flat portion parallel to the bottom face 105 and recessed portions 145. Alternatively, indentation 146 may have a dome-like cross-section, with a gradual slope from recessed portion 145 of bottom face 105 to an apex at central portion 147, and then a gradual slope back to recessed portion 145. Additionally, or alternatively, the raised surface of the indentation 146 may serve to strengthen the bottom face 105 of the container (e.g., resist twisting or warping), or facilitate manufacturing (e.g., ease removal of the container from an injection or thermoforming mold).

The bottom face 105 and recessed portions 145 may allow for the container 100 to be received in a transportation device in a plurality of orientations. As shown in FIG. 2C, a first container 200a may be receivable into a transportation device 205c via the indentations 130 in a first orientation. The transportation device 205c may be configured such that a container may not be receivable in a lower portion 205 in the first orientation. In some embodiments, the transportation device 205c may lack means for receiving a container by the indentations 130, and/or include additional elements that may otherwise prevent the first container 200a from being received, e.g., support elements at a bottom portion of the transportation device 205c. In this event, a second container 200b may be receivable into the transportation device 205c in a second orientation, e.g., rotation of the container 90° about a central axis 155. The recessed portion 145 may allow for the second container 200b to fit in the transportation device 205c with enough vertical clearance from an above first container 200a. In some embodiments, the container 100 may be formed in a rectangle, so that in the second orientation the second container 200b is receivable in a narrower configuration than in the first orientation. It is understood that the first and second containers 200a, 200b may include the features described with respect to the container 100, as described below.

Figure 1H:
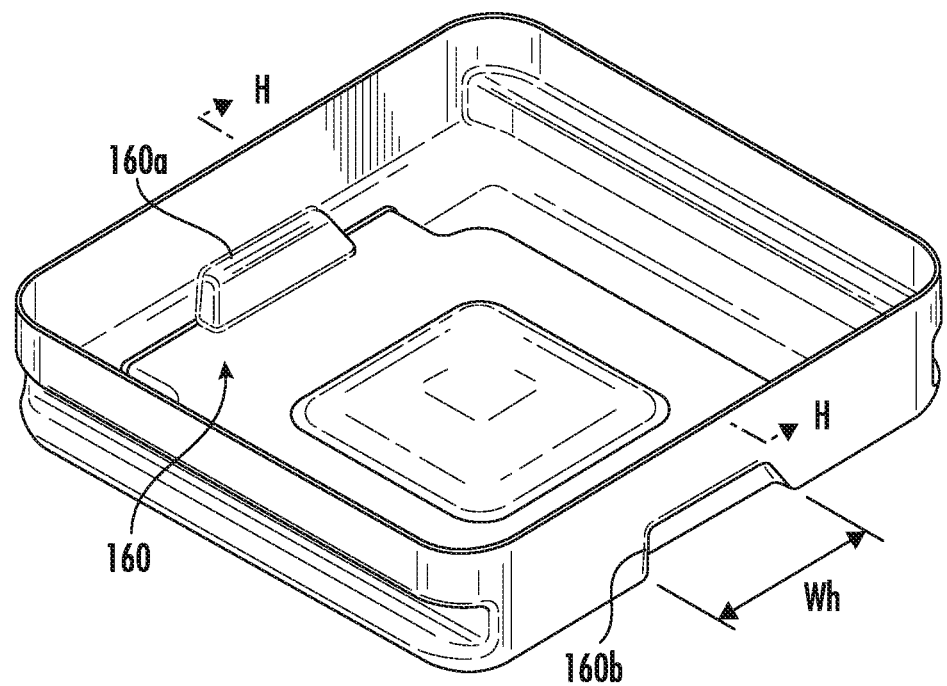
Figure 1I:
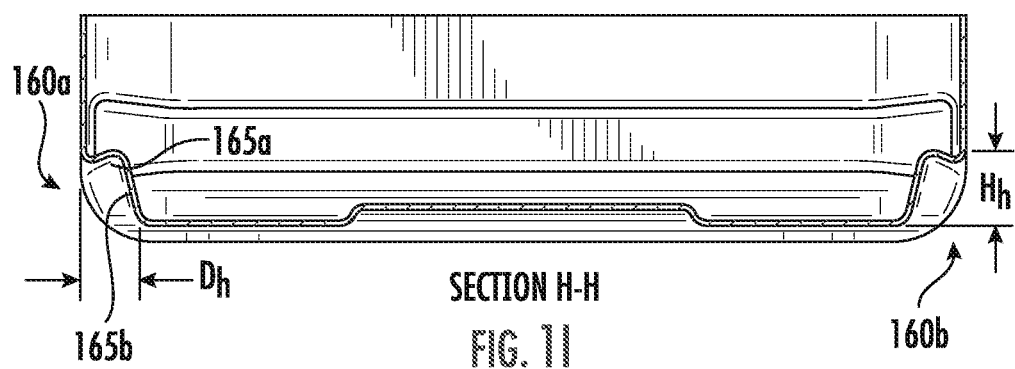
Figure 2D:
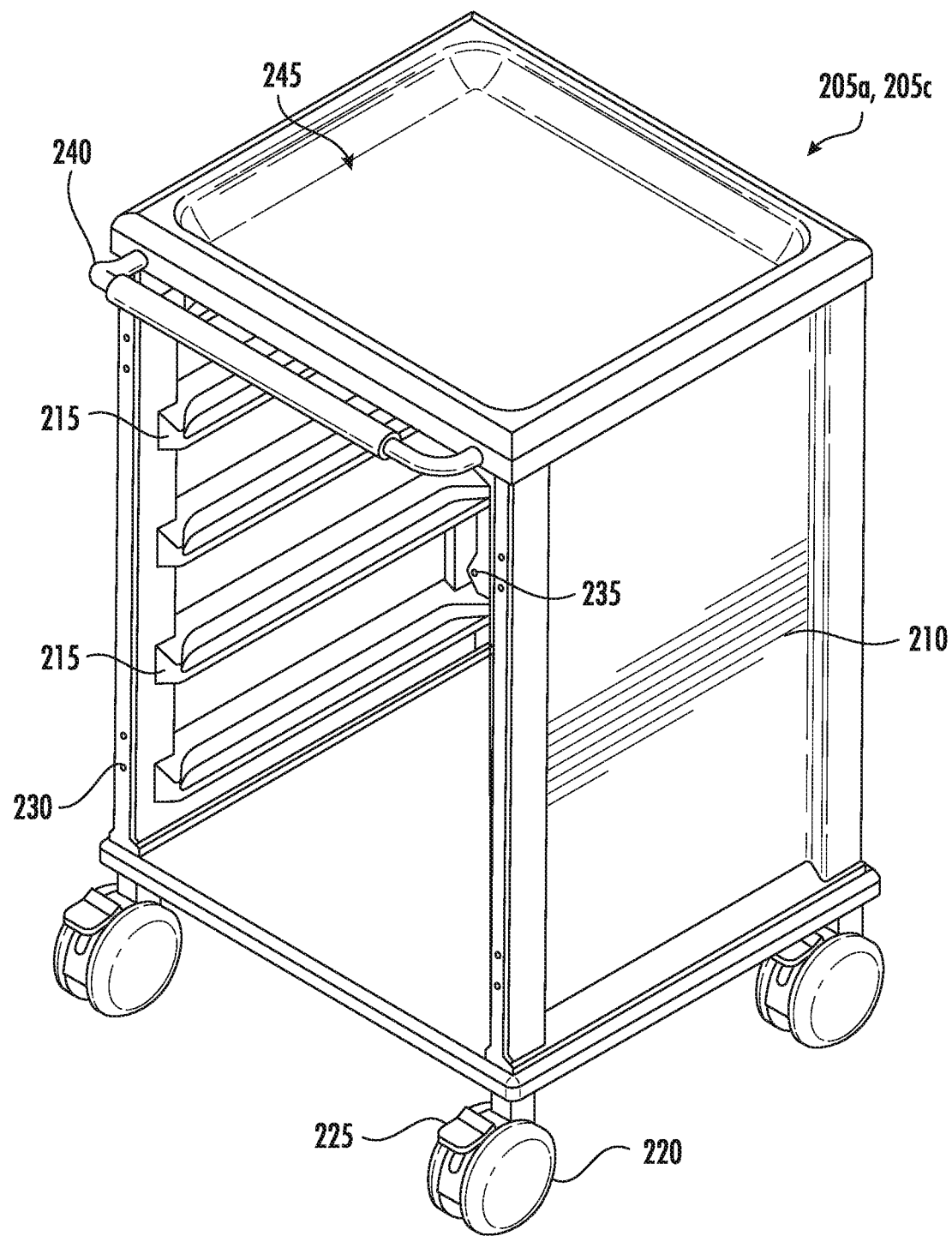

In some embodiments, the bottom face 105 and/or surrounding side faces 110a-110d, may incorporate a handle 160, 170, 180 to facilitate holding and movement of the container 100 (see FIGS. 1H-1I). Referring to FIGS. 1H-1I, a container 100 with corner handles 160 is depicted. Respective corner handles 160a, 160b may be integrated into opposite sides faces 110b, 110d, and their adjoining recessed portions 145 of bottom face 105. Each handle 160a, 160b, may have a width $W_h$, height $H_h$ and depth $D_h$ dimension that is sized to accommodate the fingers of a user's hand grasping the container palm-side upward. For example, each handle 160a, 160b, may have a width $W_h$ that extends 3-7 in. (76.2-177.8 mm), height $H_h$ that extends 1.0-3.0 in. (25.4-76.2 mm), and depth $D_h$ that extends 0.5-2.0 in. (12.7-50.8 mm). Handles 160a, 160b, may extend inward from respective side faces 110b, 110d into the inner portion 125 of the container 100, and may include a sloped vertical face 165b that transitions to a recessed dimple 165a. Dimple 165a may be sized to accommodate a user's fingertips when grasping the container 100. Other shapes and dimensions of handles 160, 170, 180 may be possible depending on user requirements. Handles 160, 170, 180 may provide a more secure grasping feature compared to holding a container from the bottom face 105 and/or side faces 110a-110d, particularly if the container is encased in a liner (e.g., liner 300 or liner 400, FIGS. 3A, 4A). For example, the handle 160a, 160b may not extend along an entire length of a side face 110a-110d.

As shown in FIG. 2B, a first container 200a may be configured to be stacked with a second container 200b, by nesting an optional lid 202 disposed on an upper surface of the second container 200b with the bottom face 105 of the first container. The first and second containers 200a, 200b may include the features described above with respect to container 100 described in relation to FIGS. 1A-1I and may be removably attachable to a respective optional lid 202. The nested configuration may allow for the containers to be stacked, e.g., vertically stacked, relative to each other, which may be advantageous for storing extra containers in a medical facility, and/or during transport of a plurality of containers. For example, the nesting configuration may provide stability to the stack of containers to reduce a likelihood of tipping over, which may reduce potential contamination of a medical device. The lid 202 may be formed of a substantially rigid material such as a plastic or composite material and may be a single piece thermoformed or molded configuration.

The containment and transportation system may further include a liner for lining the inner portion 125 of the container 100. In embodiments, a liner may be included so that when a medical device is placed in the inner portion 125 of the container 100, the liner may act as a protective barrier to the inner portion 125. This may aid in minimizing potential contamination of the container, e.g., when receiving and/or retaining a used medical device. When the medical device is removed for cleaning, the liner may be disposed of so that the container may avoid direct contact with the used medical device. In some embodiments the containment and transportation system can include one or more covers. The cover may be extendable across the second open end 120 of the container 100, so that a medical device placed in the inner portion 125 of the container is enclosed between the liner and the cover.

Figure 3A:
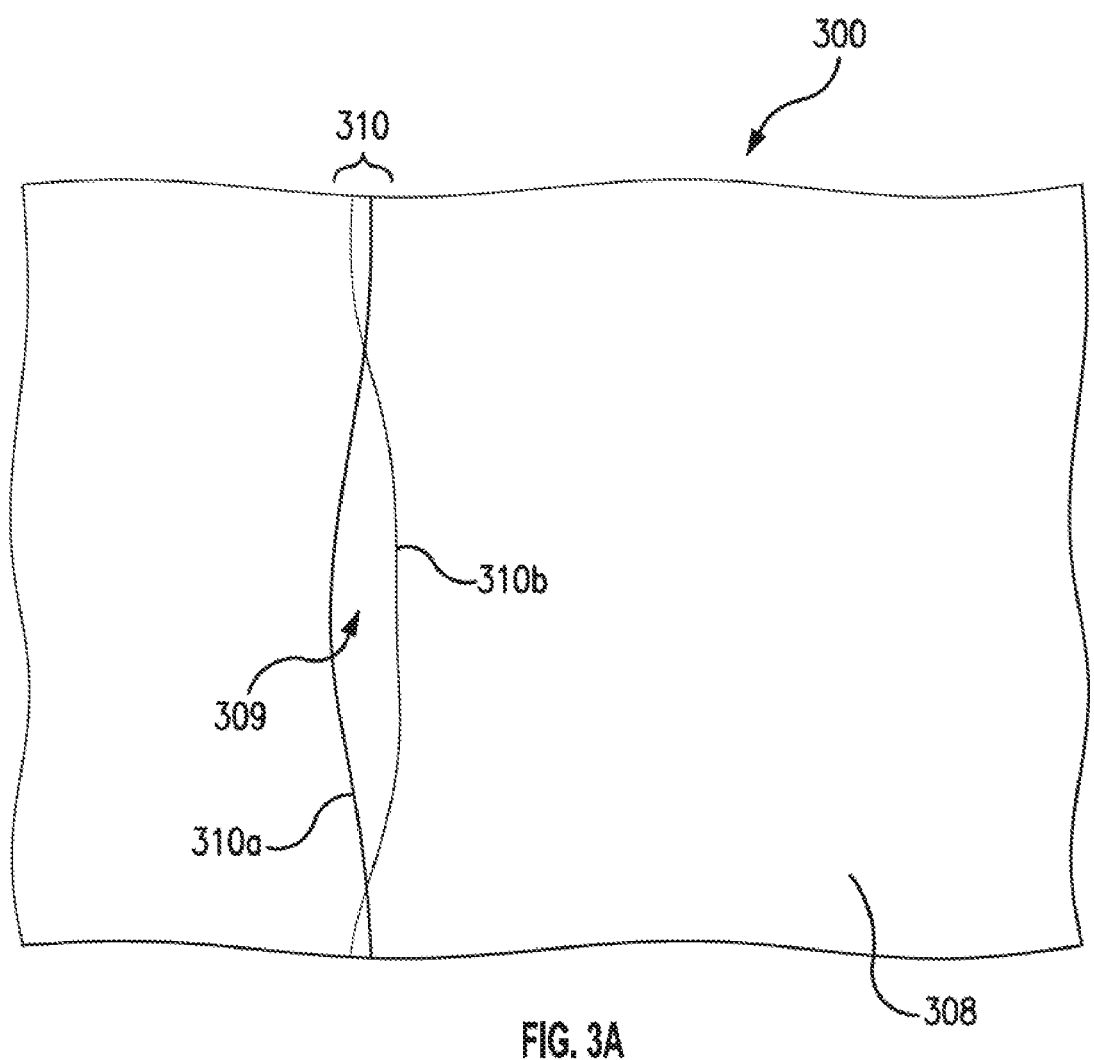
FIGS. 3A-3F illustrate exemplary embodiments of a container liner and cover in accordance with the present disclosure.
Figure 3B:
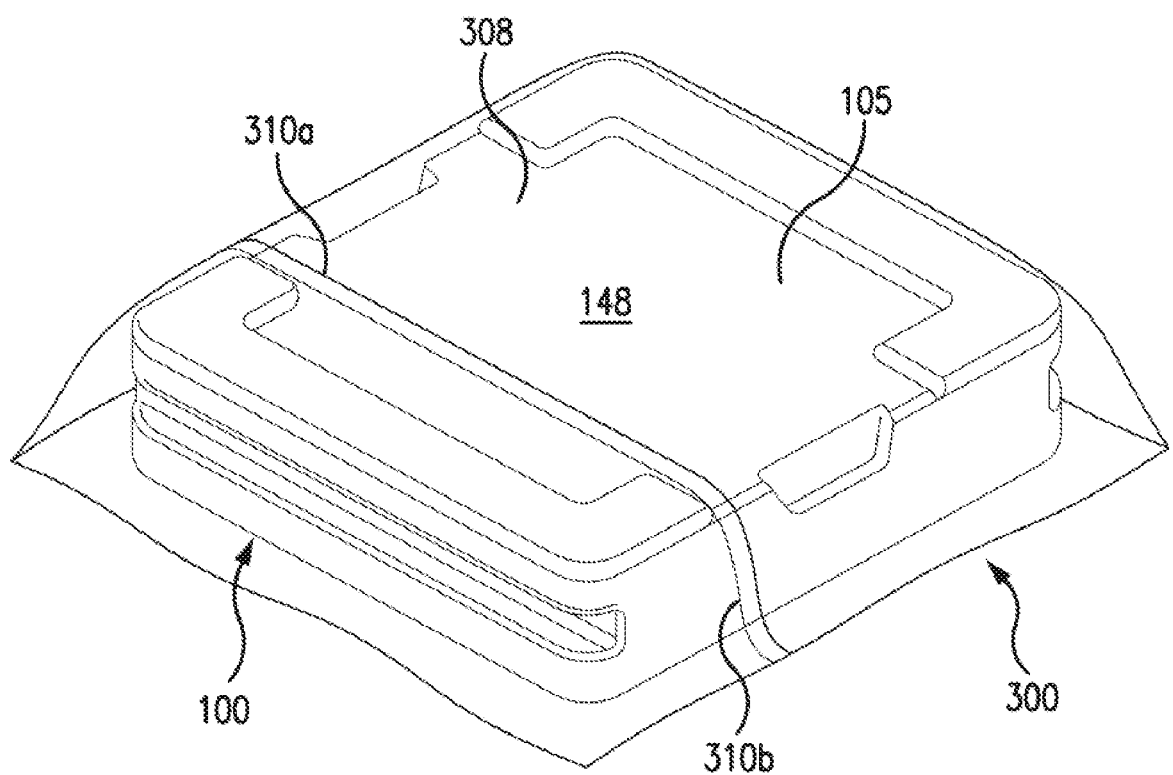
Figure 3C:
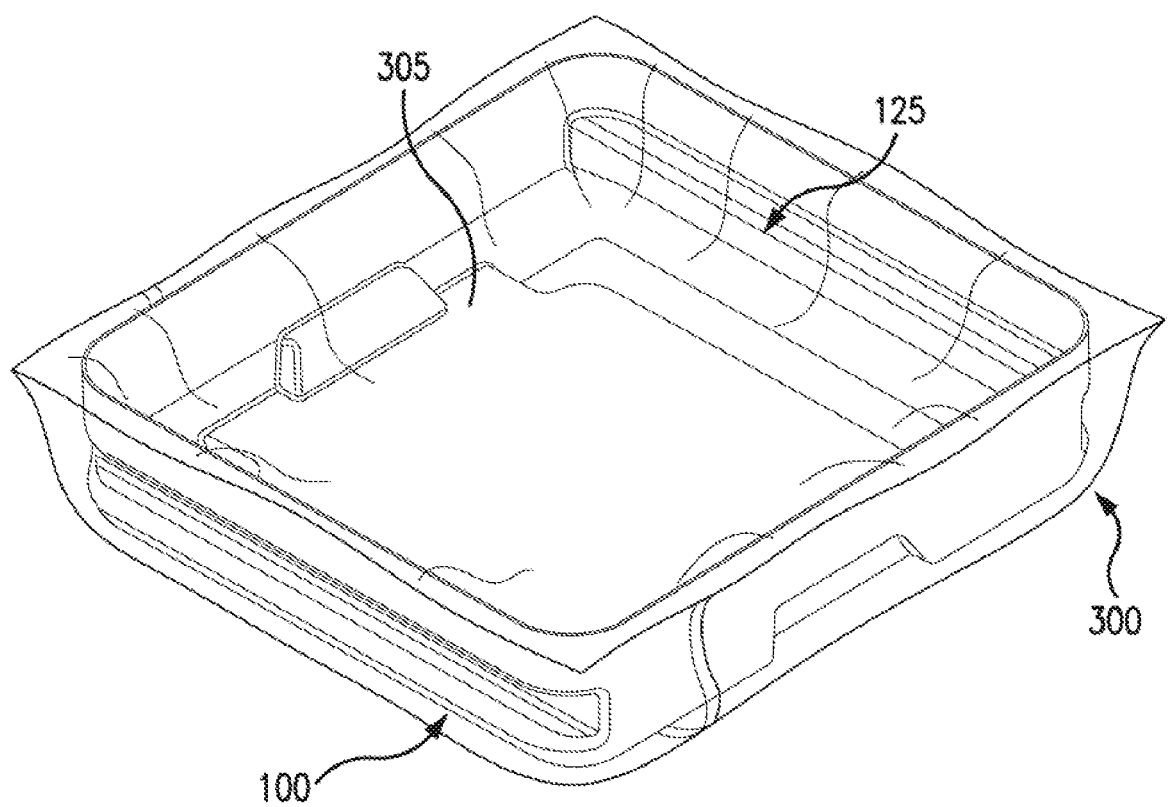

Referring now to FIGS. 3A-3F, an embodiment of a liner and first and/or second cover is described. Liner 300 may have a lining portion 305, bottom portion 308 and a closure feature 310 that together define a "pillow sham"-type enclosure 309 into which container 100 may be placed (FIG. 3A-3C). The lining portion 305 may be sized to extend over the side faces 110a-110d of the container 100 and line the inner portion 125. The lining portion 305 may be extendable fully over the side faces 110a-110d to an outer surface 148 of the bottom face 105 of the container 100. The lining portion 305 and the bottom portion 308 may fully enclose, or substantially fully enclose, the container 100, to act as a protective barrier and prevent and/or minimize direct contact between a medical device and the container, and/or between a user and the medical device and/or container (see FIG. 3B-3C). The liner 300, including the lining portion 305 and the bottom portion 308, may comprise a flexible material, such as a single piece or multiple pieces to form the enclosure 309. The flexible material may allow for the liner 300 to be conformable to a profile of the container 100, e.g., the liner may surround the side faces 110a-110d and may sit in the inner portion 125 of the container (FIG. 3C). In embodiments, the liner 300 may be at least partially substantially transparent or translucent, although it is also envisioned that the liner 300 may be colored, or opaque. The liner 300 may include symbols, textures, patterns and/or words to, e.g., indicate orientation of the tray within the liner, highlight the closure feature 310, indicate the status of the medical device at various stages of use, reprocessing, transport and handling, or the like. For example, wording such as "long side", "short side", "slit opening", or a textural cuff along the opening, may be included to allow a user to correctly orient the tray with respect the liner, and locate the opening for loading the tray into the liner.

The container may be removably enclosable within the enclosure 309 of the liner 300 by the closure feature 310, so that when the container 100 is lined, the closure feature 310 maintains the liner 300 in position and to enclose the container 100. As shown in FIG. 3B, when the liner 300 encloses the container 100, the closure feature 310 may be disposed on the outer surface 148 of the bottom face 105. By aligning the liner 300 so that the lining portion 305 is continuously extended across the inner portion 125 of the container 100, contamination of the container may be minimized. For example, fluids or other particulates may not leak or may be substantially inhibited from leaking across the edges of the closure feature 310 when positioned on the outer surface 148 of the bottom face 105.

The closure feature 310 may be an opening in the enclosure 309 extending across the width of the liner and including overlapping edges 310a and 310b of the bottom portion 308 of the liner 300 (FIG. 3A-3B). The opening may comprise individual pieces of connected flexible material, e.g., one piece of material as the lining portion 305 that extends the length of the liner and two pieces of material as the bottom portion 308 positioned on top of the lining portion with aligned and connected outer edges defining the outer perimeter of the enclosure 309. Respective overlapping edges 310a and 310b may be included a distance along the length of the liner as the opening at closure feature 310. In embodiments, the closure feature 310 may be an opening in the enclosure 309 extending across the width of the liner and including edges 310a and 310b of the bottom portion 308 of the liner 300 that are adjacent, but not overlapping. The edges of the short side and long side may be aligned adjacent to each other as the opening of closure feature 310 with respective short side and long side edges 310a, 310b, and the outer edges may be aligned and connected, as above, as the outer perimeter of the enclosure 309.

The edges 310a and 310b of the opening at closure feature 310 may be separated to load container 100 upside down within enclosure 309. One end of the container may be slid under edge 310b into the larger portion of the enclosure 309, and then the remaining smaller portion of the enclosure 309 may be pulled around and over the other end of the container, such that edge 310a overlaps 310b to close the opening at closure feature 310 (FIG. 3B). The positioning of the closure feature 310 along the length of the bottom portion 308 of the liner, and the degree of overlap of edges 310a, 310b, may be varied as desired. By fully enclosing or substantially fully enclosing the container 100 within the liner 300, leaving little or no portion of an underside of the container exposed, contamination of the container and/or clean medical device may be minimized.

As described, the container 100 may be removably enclosed within the liner 300 prior to placement of a medical device in the inner portion 125 of the container. A medical device may be placed in an inner portion 125 of a container 100 after the container is enclosed within the liner 300.

Figure 3D:
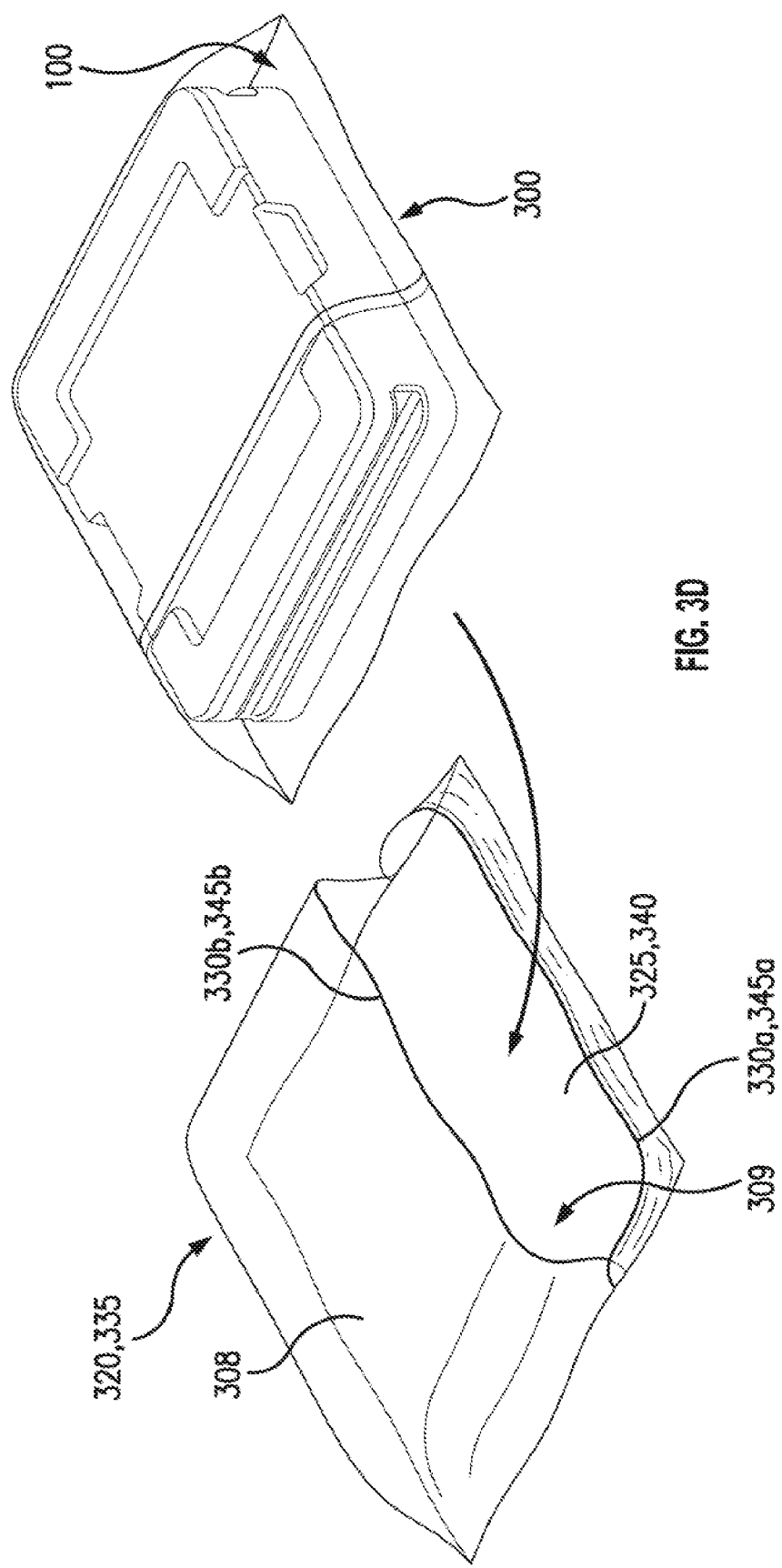
Figure 3E:
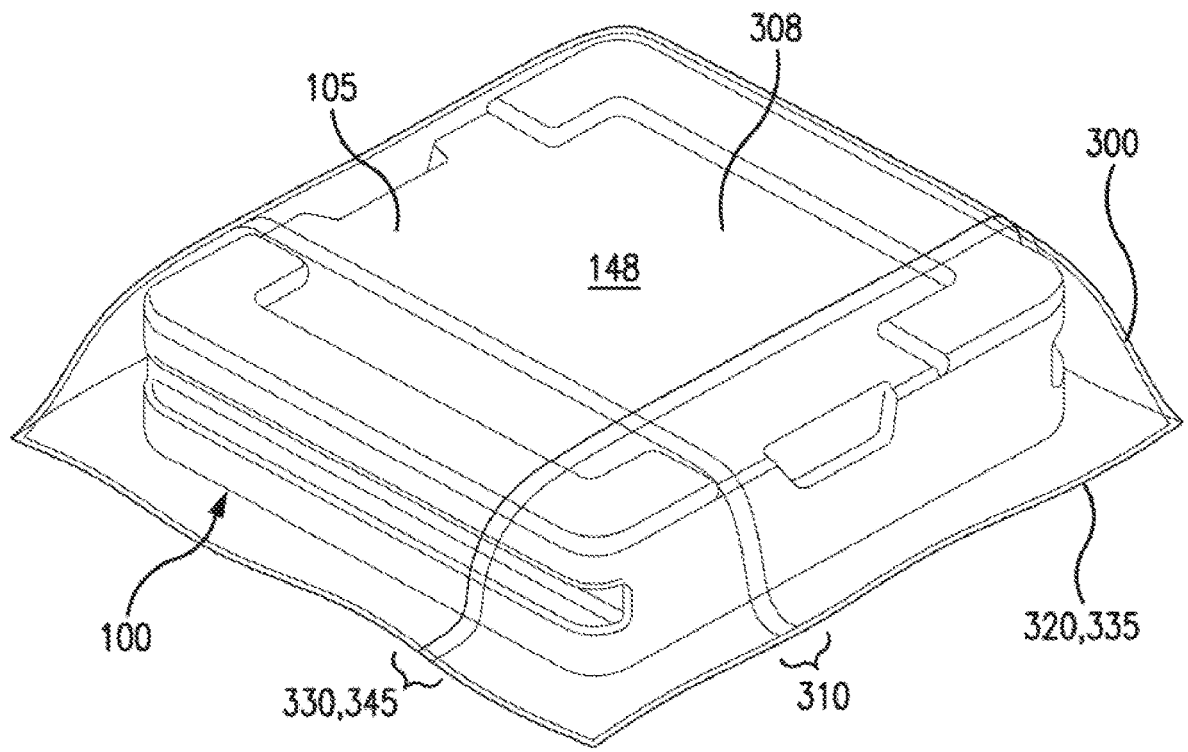
Figure 3F:
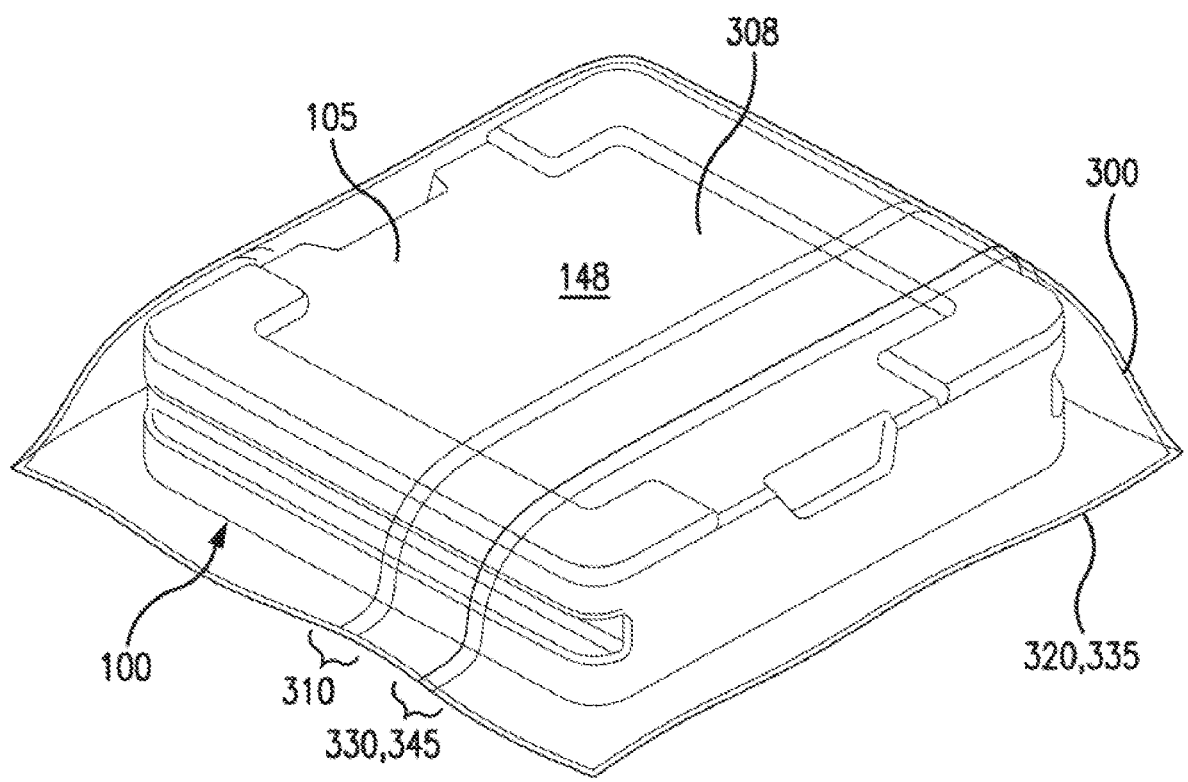

When the medical device is placed in the container, a cover may be extendable across the second open end 120, so that the medical device is captured between the liner 300 and a cover 320, 335. Referring to FIGS. 3D-3F, a first cover 320 may have a cover portion 325, bottom portion 308 and a closure feature 330 defining an enclosure 309, and a second cover 335 may have a cover portion 340, bottom portion 308 and a closure feature 345 defining an enclosure 309. Closure features 330, 345 may be an opening in the enclosure 309 extending across the width of the respective covers 320, 335, and including respective overlapping edges 330a, 330b and 345a, 345b of the bottom portion 308 (FIG. 3D). The cover portions 325, 340, bottom portions 308 and closure features 330, 345 may define enclosure 309, as described above with respect to liner 300.

The flexible material may allow for the first and second cover 320, 335 to extend across the container 100, e.g., the first and/or second cover 320, 335 may form a barrier across the second open end 120 of the container 100. In embodiments, the first and/or second cover 320, 335 may be at least partially substantially transparent or translucent. It is also envisioned that the first and second covers 320, 335 may be different colors, and/or may include symbols, textures, patterns and/or words to, e.g., indicate orientation of the tray within the cover, highlight the closure feature 330, 345, indicate the status of the medical device at various stages of use, reprocessing, transport and handling, or the like. For example, wording such as "long side", "short side", "slit opening", or a textural cuff along the opening, may be included to allow a user to correctly orient the tray with respect the cover, and locate the opening for loading the tray into the cover. Different colors and/or patterns may provide an easy indicator for medical professionals traversing through a medical facility, picking up used medical devices and/or delivering clean medical devices, so that incorrect delivery of a medical device is minimized. In embodiments, the liner 300, first cover 320 and/or second cover 335 may include a section for writing on the top surface. Details regarding the medical device may be included by a medical profession, e.g., to document details such as the time the medical device was used, to track a time from use to cleaning. In some medical facilities, a used medical device must be reprocessed within a predetermined time period, such as less than 1 hour. In embodiments, the first cover 320 may be different than the second cover 335, so that a medical professional may have a visual indication of a condition of the medical device in the container 100. For example, a green colored cover 320 may indicate a clean medical device. A medical professional may be able see the green cover 320 and transport the medical device to a patient procedure location for use. Similarly, a red colored cover 335 may indicate a used medical device, so the medical professional may transport the medical device to a reprocessing location. In some embodiments, a hazardous waste symbol, and/or a pattern of hazardous waste symbols, may be included on a cover 335 to indicate a used medical device, so that the pattern may indicate to a medical professional for proper handling and disposal. Alternatively, the first cover may be reversible, as opposed to having a second cover, with each side of the reversible cover for visual verification of a different condition of the medical device. For example, after endoscope reprocessing, a clean medical device may be placed in a lined container, and a reversible cover 320 with opposing sides that are green and red may be extended across the second open end 120, with the green side facing upwards providing a visual verification of the clean condition of the endoscope. The container may be transported from a reprocessing location to a medical procedure location, where the clean medical device may be used on a patient. Subsequent to the procedure, the used medical device may be placed back in the container, and the reversible cover 320 may be extended across the second open end 120, with the red side facing upwards providing a visual verification of the used condition of the endoscope. This may indicate to a medical professional, or other medical facility personnel that the medical device should be transported back to the reprocessing area for cleaning. Similarly, opposing sides of a reversible cover may include symbols, patterns and/or words to indicate the status of the medical device at various stages of use, reprocessing, transport and handling.

The container 100 enclosed within liner 300 may be removably enclosable within enclosure 309 of the cover 320, 335 by the closure feature 330, 345 (FIG. 3D). The closure feature 330, 345 may be an opening in the enclosure 309 extending across the width of the cover and including overlapping edges 330*a*, 330*b* and 345*a*, 345*b* of the bottom portion 308 of respective covers 320, 335 (FIG. 3D). In embodiments, the closure feature 330, 345 may be an opening in the enclosure 309 extending across the width of the cover and including 330*a*, 330*b* and 345*a*, 345*b* of the bottom portion 308 of respective covers 320, 335 that are adjacent, but not overlapping. The edges of the opening at closure feature 330, 345 may be separated to load container 100 upside down within enclosure 309 in the same fashion as described above for liner 300. The position of the closure feature 330, 345 along the length of the bottom portion 308 of the cover, and the degree of overlap of edges 330*a*, 330*b* and 345*a*, 345*b*, may be varied as desired.

As shown in FIGS. 3E and 3F, when the cover 320, 335 encloses the container 100, the closure feature 330, 345 may be disposed on the outer surface 148 of the bottom face 105. By aligning the cover 320, 335 so that the cover portion 325, 340 is continuously extended across the inner portion 125 of the container 100, contamination of the container may be minimized. For example, fluids or other particulates may not leak or may be substantially inhibited from leaking across the closure feature edges 330*a*, 330*b* and 345*a*, 345*b*, when positioned on the outer surface 148 of the bottom face 105. To further inhibit leaking, the container can be loaded into the liner and the cover such that the closure features of the liner and cover are cross-wise (e.g., substantially perpendicular) to each other, rather than parallel, as shown in FIG. 3E. In other embodiments, to further inhibit leaking, the container can be loaded into the liner and the cover such that the closure features of the liner and cover are parallel and staggered, as shown in FIG. 3F. Crossing and/or staggering the closure features of the liner and cover may create a more tortuous path that reduces or eliminates the possibility of fluids or other particulates leaking via both openings of the liner and cover to potentially contaminate a workspace or other systems. In embodiments, corresponding ones of edges 310*a*, 310*b*, 330*a*, 330*b*, 345*a*, 345*b* of closure features 310, 330, 345 may at least partially overlap, abut, overlay, underlay, adjoin, or any combination thereof.

By fully enclosing or substantially fully enclosing the container 100 within the covers 320, 335, leaving little or no portion of an underside of the container exposed, contamination of the container and/or clean medical device may be minimized.

Figure 4A:
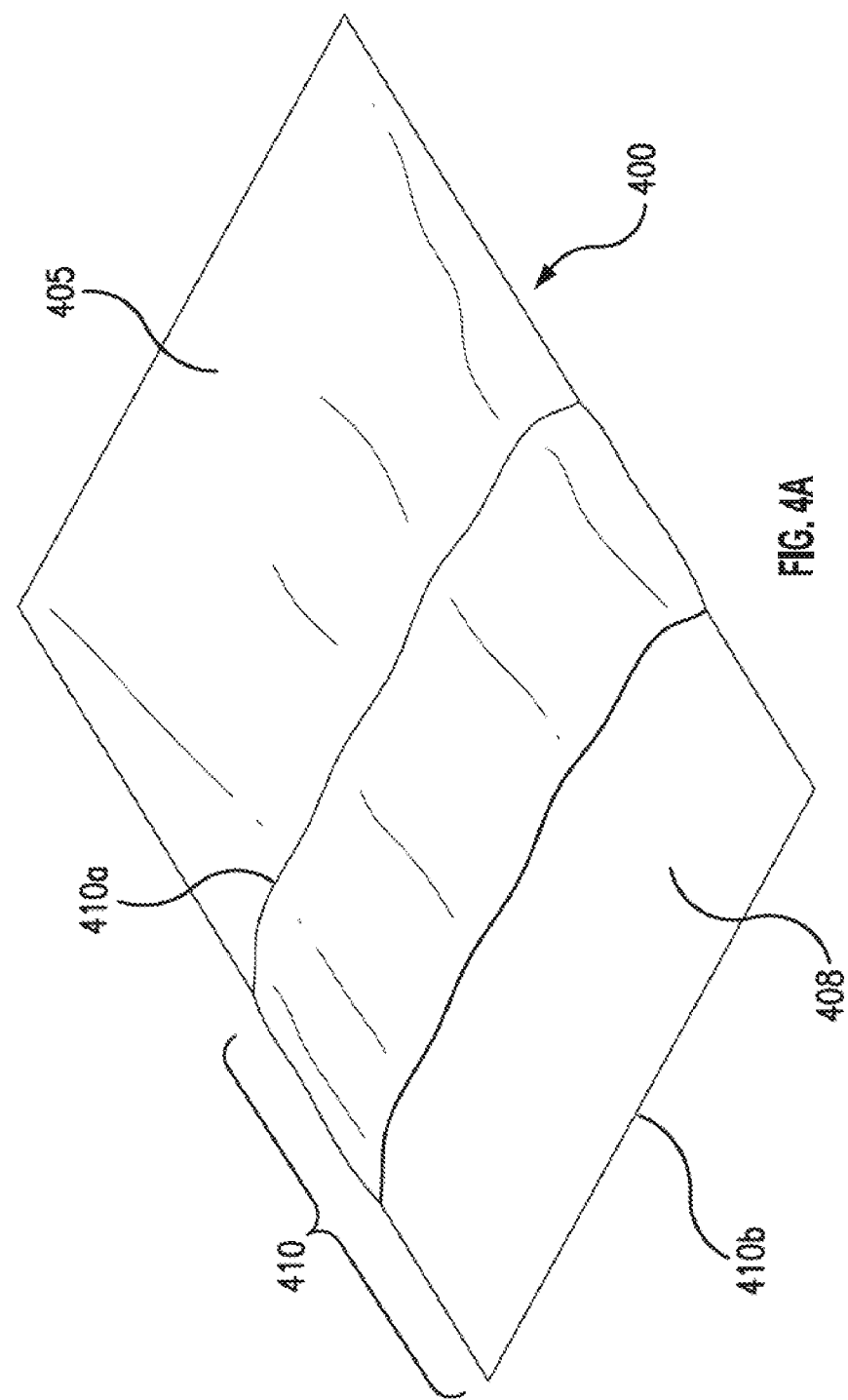
Figure 4B:
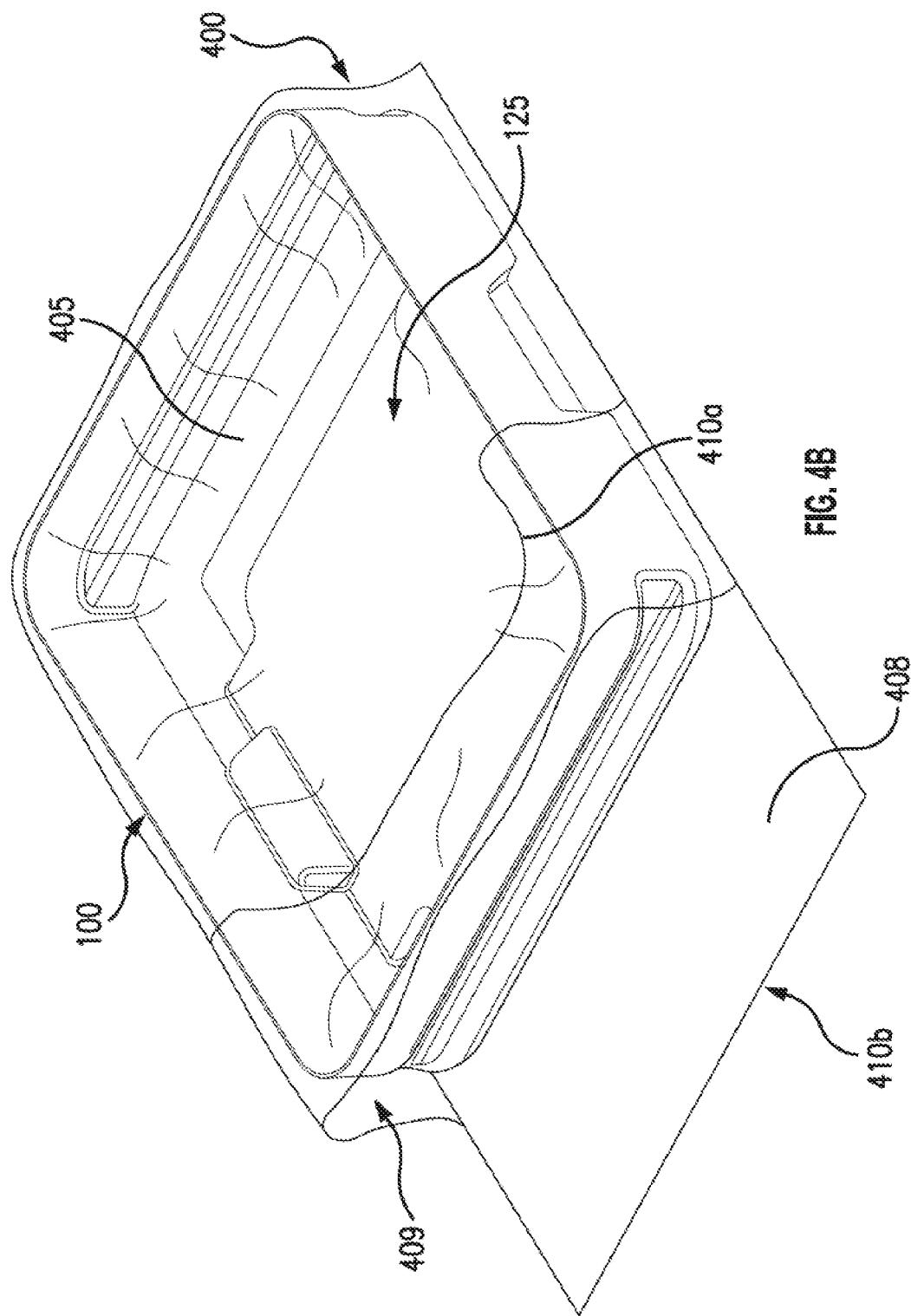
Figure 4C:
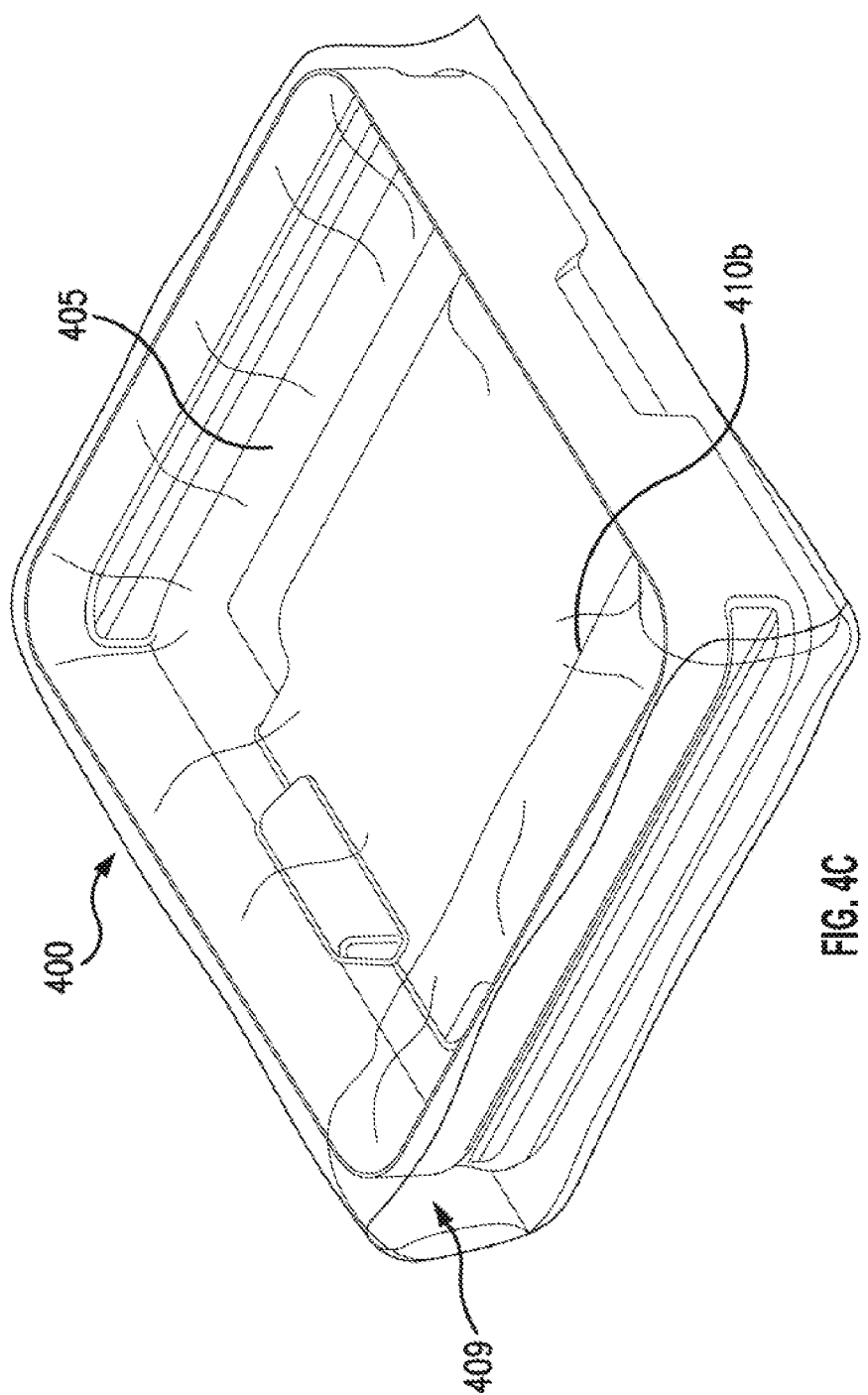

Referring now to FIGS. 4A-4E, an alternative embodiment of a liner and first and/or second cover is described. Liner 400 may have a lining portion 405, bottom portion 408 and a closure feature 410 that together define a "sandwich bag"-type enclosure 409 into which container 100 may be placed (FIG. 4A-4D). The lining portion 405 may be sized to extend over the side faces 110*a*-110*d* of the container 100 and line the inner portion 125. The lining portion 405 may be extendable fully over the side faces 110*a*-110*d* to an outer surface 148 of the bottom face 105 of the container 100. The lining portion 405 and the bottom portion 408 may fully enclose, or substantially fully enclose, the container 100, to act as a protective barrier and prevent and/or minimize direct contact between a medical device and the container, and/or between a user and the medical device and/or container (see FIG. 4B-4D). The liner 400, including the lining portion 405 and the bottom portion 408, may comprise a flexible material, such as a single piece or multiple pieces to form the enclosure 409. The flexible material may allow for the liner 400 to be conformable to a profile of the container 100, e.g., the liner may surround the side faces 110*a*-110*d* and may sit in the inner portion 125 of the container (FIG. 4B-4C). In embodiments, the liner 400 may be at least partially substantially transparent or translucent, although it is also envisioned that the liner 400 may be colored, or opaque. The liner 400 may include symbols, textures, patterns and/or words to, e.g., indicate orientation of the tray within the liner, highlight the closure feature 410, indicate the status of the medical device at various stages of use, reprocessing, transport and handling, or the like. For example, wording such as "opening", or a textural feature along the opening, may be included to allow a user to correctly orient the tray with respect the liner, and locate the opening for loading the tray into the liner.

The container may be removably enclosable within the enclosure 409 of the liner 400 by the closure feature 410, so that when the container 100 is lined, the closure feature 410 maintains the liner 400 in position and to enclose the container 100. As shown in FIG. 4D, when the liner 400 encloses the container 100, the closure feature 410 may be disposed on the outer surface 148 of the bottom face 105. By aligning the liner 400 so that the lining portion 405 is continuously extended across the inner portion 125 of the container 100, contamination of the container may be minimized. For example, fluids or other particulates may not leak or may be substantially inhibited from leaking across the edges of the closure feature 410 when positioned on the outer surface 148 of the bottom face 105.

The closure feature 410 may be an opening in the enclosure 409 extending across the width of the liner and including cuff edge 410a of the lining portion 405 and flap edge 410b of the bottom portion 408 of the liner 400 (FIG. 4A-4B).

The flap edge 410b and cuff edge 410a of the opening at closure feature 410 may be separated to load container 100 right side up within enclosure 409. The container may be fully slid into enclosure 409 under the cuff edge 410a and lining portion 405 and on top of the bottom portion 408 (FIG. 4B). The flap edge 410b may then be tucked into enclosure 409 and the cuff with edge 410a may be turned inside out and inverted over the flap edge 410b and around the end of container 100 to secure the container within the liner 400 (FIG. 4C). In the closed position, flap edge 410b may extend within inner portion 125 of the container with lining portion 405 lining the container, and cuff edge 410a may extend across the width of liner 400 on the bottom face 105 of the container (FIGS. 4C-4D). The position of the closure feature 410 along the length of the bottom portion 408 of the liner, and the extent of edges 410a, 410b, may be varied as desired. The orientation of the container within the enclosure 409, and the interaction between cuff edge 410a and flap edge 410b may be varied as well. For example, the container may be loaded upside down into enclosure 409, which would make the material layer with flap edge 410b the lining portion 405 and the material layer with cuff edge 410a the bottom portion 408. When closed, cuff edge 410a may be inverted over flap edge 410b and may extend across the width of the lining portion 405 of liner 400. As a further example, instead of flap edge 410b being tucked into enclosure 409, flap edge 410b may be folded over cuff edge 410a, and cuff edge 410a may be turned inside out and inverted over flap edge 410b and around the end of container 100 to secure the container within the liner 400.

By fully enclosing or substantially fully enclosing the container 100 within the liner 400, leaving little or no portion of the container exposed, contamination of the container and/or clean medical device may be minimized.

As described, the container 100 may be removably enclosed within the liner 400 prior to placement of a medical device in the inner portion 125 of the container. A medical device may be placed in the inner portion 125 of the container 100 after the container is enclosed within the liner 400.

Figure 4E:
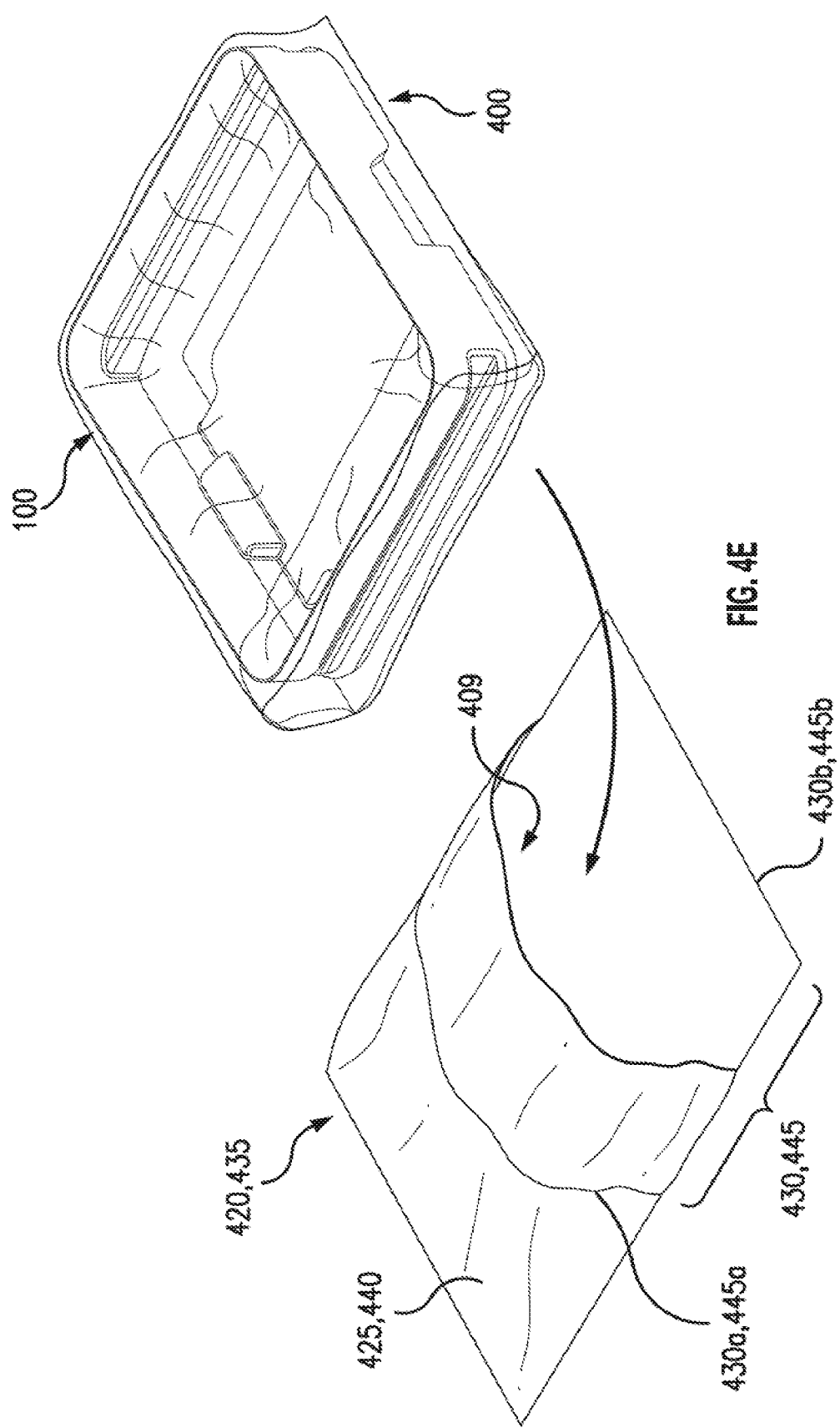
Figure 4F:
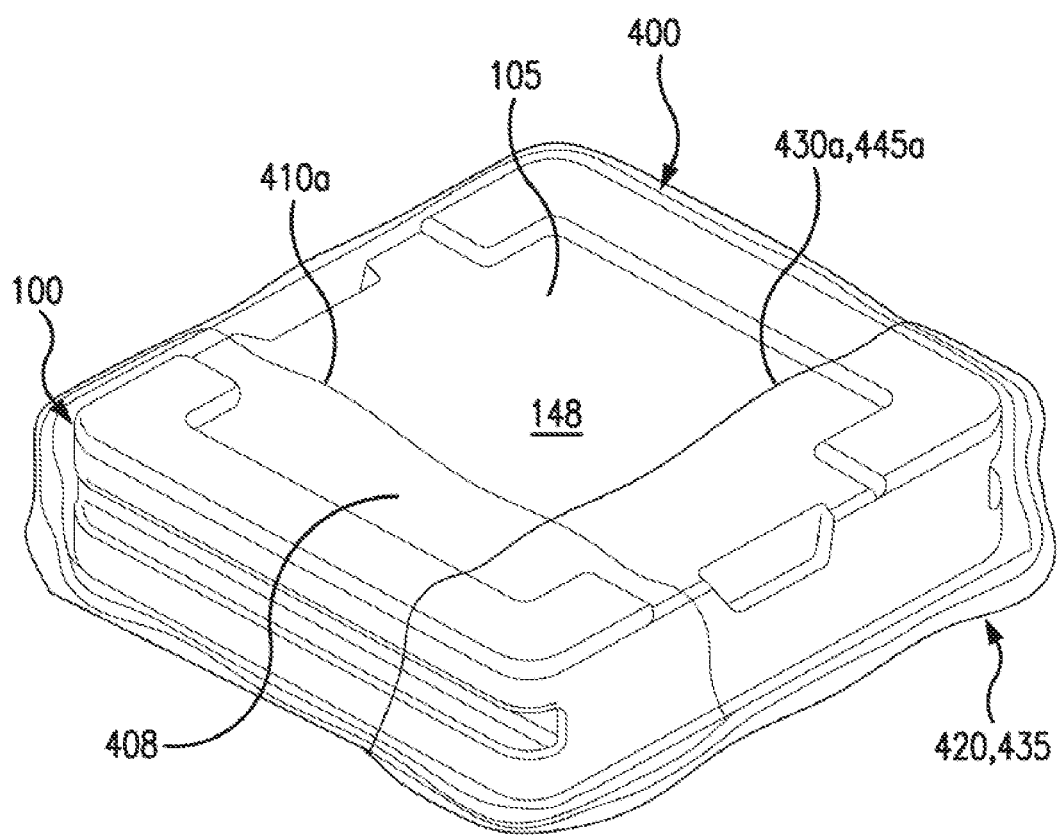
Figure 4G:
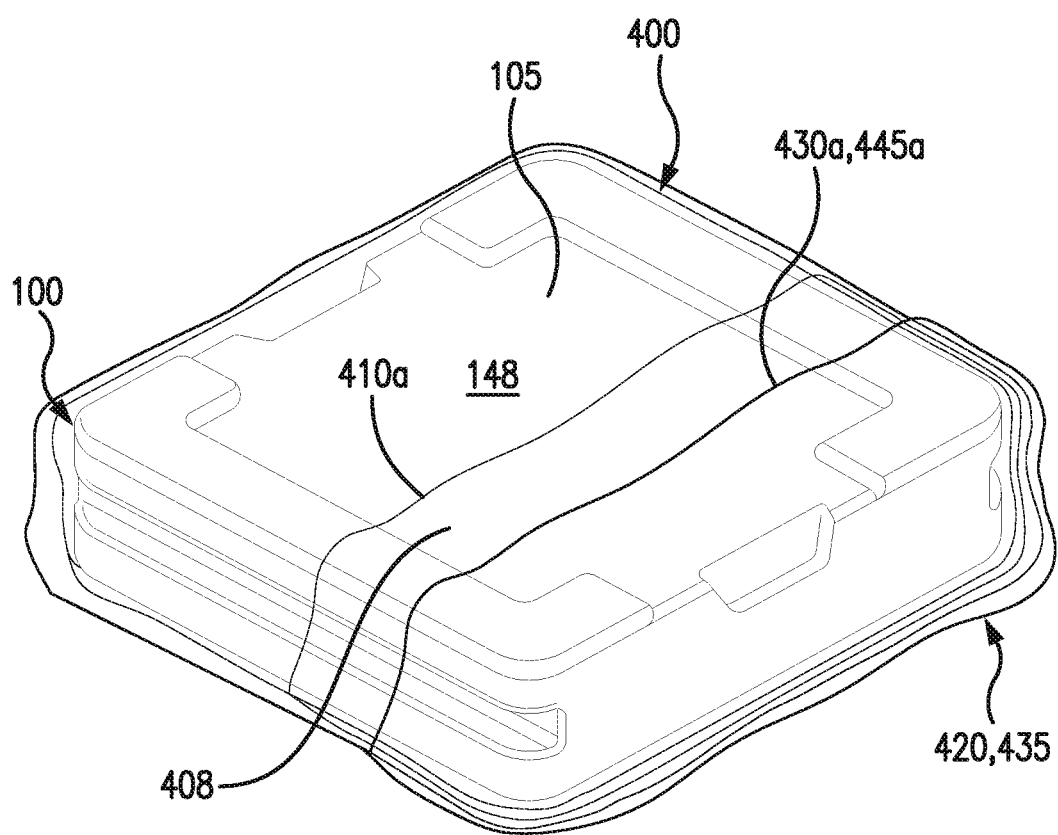

When the medical device is placed in the container, a cover may be extendable across the second open end 120, so that the medical device is captured between the liner 400 and a cover 420, 435. Referring to FIGS. 4E-4G, a first cover 420 may have a cover portion 425, bottom portion 408 and a closure feature 430 defining an enclosure 409, and a second cover 435 may have a cover portion 440, bottom portion 408 and a closure feature 445 defining an enclosure 409, each in the manner of a "sandwich bag"-type enclosure similar to liner 400. Closure features 430, 445 may be an opening in the enclosure 409 extending across the width of the respective covers 420, 435, and including respective cuff edges 430a, 445a of the cover portion 425, 440 and respective flap edges 430b, 445b of the bottom portion 408 (FIG. 4E). The cover portions 425, 440, bottom portions 408 and closure features 430, 445 may define enclosure 409, as described above with respect to liner 400.

The covers 420, 435, including the cover portions 425, 440 and the bottom portion 408 and the closure features 430, 445 may comprise a flexible material, such as a single piece or multiple pieces to form the enclosure 409. The flexible material may allow for the first and second cover 420, 435 to extend across the container 100, e.g., the first and/or second cover 420, 435 may form a barrier across the second open end 120 of the container 100. In embodiments, the first and/or second cover 420, 435 may be at least partially substantially transparent or translucent. It is also envisioned that the first and second covers 420, 435 may be different colors, and/or may include symbols, textures, patterns and/or words to, e.g., indicate orientation of the tray within the cover, highlight the closure feature 430, 445, indicate the status of the medical device at various stages of use, reprocessing, transport and handling, or the like. For example, wording such as "opening", or a textural feature along the opening, may be included to allow a user to correctly orient the tray with respect the cover, and locate the opening for loading the tray into the cover. Different colors and/or patterns may provide an easy indicator for medical professionals traversing through a medical facility, picking up used medical devices and/or delivering clean medical devices, so that incorrect delivery of a medical device is minimized. In embodiments, the liner 400, first cover 420 and/or second cover 435 may include a section for writing on the top surface. Details regarding the medical device may be included by a medical professional, e.g., to document details such as the time the medical device was used, to track a time from use to cleaning. In some medical facilities, a used medical device must be reprocessed within a predetermined time period, such as less than 1 hour. In embodiments, the first cover 420 may be different than the second cover 435, so that a medical professional may have a visual indication of a condition of the medical device in the container 100. For example, a green colored cover 420 may indicate a clean medical device. A medical professional may be able see the green cover 420 and transport the medical device to a patient procedure location for use. Similarly, a red colored cover 435 may indicate a used medical device, so the medical professional may transport the medical device to a reprocessing location. In some embodiments, a hazardous waste symbol, and/or a pattern of hazardous waste symbols, may be printed on a cover 435 to indicate a used medical device, so that the pattern may indicate to a medical professional for proper handling and disposal. Alternatively, the first cover may be reversible, as opposed to having a second cover, with each side of the reversible cover for visual verification of a different condition of the medical device. For example, after endoscope reprocessing, a clean medical device may be placed in a lined container, and a reversible cover 420 with opposing sides that are green and red may be extended across the second open end 120, with the green side facing upwards providing a visual verification of the clean condition of the endoscope. The container may be transported from a reprocessing location to a medical procedure location, where the clean medical device may be used on a patient. Subsequent to the procedure, the used medical device may be placed back in the container, and the reversible cover 420 may be extended across the second open end 120, with the red side facing upwards providing a visual verification of the used condition of the endoscope. This may indicate to a medical professional, or other medical facility personnel that the medical device should be transported back to the reprocessing area for cleaning. Similarly, opposing sides of a reversible cover may include symbols, patterns and/or words to indicate the status of the medical device at various stages of use, reprocessing, transport and handling.

The container 100 enclosed within liner 400 may be removably enclosable within enclosure 409 of the cover 420, 435 by the closure feature 430, 445 (FIG. 4E). The closure feature 430, 445 may be an opening in the enclosure 409 extending across the width of the cover and including cuff edges 430a, 445a and flap edges 430b, 445b of the respective covers 420, 435 (FIG. 4E). The edges of the opening at closure feature 430, 445 may be separated to load container 100 right side up within enclosure 409 in the same fashion as described above for liner 400. The position of the closure feature 430, 445 along the length of the bottom portion 408, the dimensions of cuff edges 430a, 445a and flap edges 430b, 445b, the orientation of the container within the enclosure 409, and the interaction between cuff edges 430a, 445a and flap edges 430b, 445b, may be varied as described above for liner 400.

As shown in FIGS. 4F and 4G, when the cover 420, 435 encloses the container 100, the closure feature 430, 445 may be disposed with cuff edges 430a, 445a on the outer surface 148 of the bottom face 105. By aligning the cover 420, 435, so that the cover portion 425, 440 is continuously extended across the inner portion 125 of the container 100, contamination of the container may be minimized. For example, fluids or other particulates may not leak or may be substantially inhibited from leaking across the closure feature cuff edges 430a, 445a and flap edges 430b, 445b, when positioned on the outer surface 148 of the bottom face 105. To further inhibit leaking, the container can be loaded into the liner and the cover such that the closure features of the liner and cover are cross-wise (e.g., substantially perpendicular) to each other, rather than parallel, as shown in FIG. 4F. In other embodiments, to further inhibit leaking, the container can be loaded into the liner and the cover such that the closure features of the liner and cover are parallel and staggered, as shown in FIG. 4G. Crossing and/or staggering the closure features of the liner and cover may create a more tortuous path that reduces or eliminates the possibility of fluids or other particulates leaking via both openings of the liner and cover to potentially contaminate a workspace or other systems. In embodiments, corresponding ones of edges 410a, 410b, 430a, 430b, 445a, 445b of closure features 410, 430, 445 may at least partially overlap, abut, overlay, underlay, adjoin, or any combination thereof.

By fully enclosing or substantially fully enclosing the container 100 within the liner 400 and cover 420 or cover 435, leaving little or no portion of the underside of the container exposed, contamination of the container and/or clean medical device may be minimized.

Additional liner and/or cover features may be relevant to aspects of the embodiments herein, as described in more detail in U.S. Patent Application, filed even date herewith, and titled "Medical Device Transportation Systems," the entirety of which application is incorporated by reference herein.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for containing and transporting a medical device, the system comprising:
   a container including a bottom face and surrounding first, second, third, and fourth side faces as a closed first end and an open second end to form an inner portion for receiving and retaining the medical device, the first and third side faces opposite each other, at least a portion of the first and third side faces each having an indentation extending along an entire length of the respective side face from the second side face to the fourth side face; and
   a liner comprising a top portion, a first bottom portion, a second bottom portion, and a closure feature, the liner configured to receive the container and to removably and fully enclose the container, the top portion of the liner being extendable over the side faces to line the inner portion of the container, such that the liner is conformable to a profile of the container;
   wherein the indentations are formed into the inner portion of the container and are configured such that the container is compatibly receivable in a first transportation device in a first orientation in which portions of the first transportation device are received in each of the indentations, and
   wherein the closure feature comprises an opening in the liner that extends across a width of the liner, the opening defined by adjacent edges of the first bottom portion and the second bottom portion of the liner.

2. The system according to claim 1, wherein the bottom face of the container includes a recess extending from the second side face to the opposite fourth side face, such that the container is compatibly receivable in the first transportation device in a second orientation different from the first orientation in which a portion of the first transportation device is received in the recess.

3. The system according to claim 1, wherein the container includes one or more handles.

4. The system according to claim 1, further comprising:
a first cover configured to removably enclose the container and to extend over at least a portion of the side faces and across the open second end of the container to enclose the inner portion; and
a second cover configured to removably enclose the container and to extend over at least a portion of the side faces and across the open second end of the container to enclose the inner portion;
wherein the first cover is exchangeable with the second cover for visual verification of a condition of the medical device.

5. The system according to claim 1, wherein the container is compatibly receivable in a second transportation device, the second transportation device differing from the first transportation device, such that the container is exchangeable between the first transportation device and the second transportation device.

6. The system according to claim 4, wherein the first cover comprises a first cover top portion, a first cover first bottom portion, a first cover second bottom portion, and a first cover closure feature, wherein the first cover is removably enclosable about the container, and wherein the first cover closure feature comprises an opening that extends across a width of the first cover and includes overlapping edges of the first cover first bottom portion and the first cover second bottom portion.

7. The system according to claim 6, wherein the second cover comprises a second cover top portion, a second cover first bottom portion, a second cover second bottom portion, and a second cover closure feature, wherein the second cover is removably enclosable about the container, and wherein the second cover closure feature comprises an opening that extends across a width of the second cover and includes overlapping edges of the second cover first bottom portion and the second cover second bottom portion.

8. A container for containing and transporting a medical device, comprising:
a bottom face and surrounding first, second, third, and fourth side faces as a closed first end and an open second end to form an inner portion for receiving and retaining the medical device, the first and third side faces opposite each other, the bottom face including a contour that comprises a recessed portion positioned along a central portion of the bottom face, wherein the recessed portion extends from the second side face to the opposite fourth side face; and
at least a portion of the first and third side faces each having an indentation extending along an entire length of the respective side face from the second side face to the fourth side face;
wherein the indentations on the at least a portion of the one or more first and third side faces are formed into the inner portion of the container; and
wherein the container is configured to be received in a first transportation device in a first orientation in which portions of the first transportation device are received in each of the indentations.

9. The container according to claim 8, further comprising a liner for removably enclosing the container, the liner being extendable over the side faces to line the inner portion of the container, such that the liner is conformable to a profile of the container.

10. The container according to claim 9, further comprising:
a first cover for removably enclosing the container, the first cover extendable over at least a portion of the side faces and across the open second end of the container to enclose the inner portion; and
a second cover for removably enclosing the container, the second cover extendable over at least a portion of the side faces and across the open second end of the container to enclose the inner portion;
wherein the first cover is exchangeable with the second cover.

11. The container according to claim 9, wherein the liner comprises a top portion, a first bottom portion, a second bottom portion, and a closure feature, the closure feature comprising an opening in the liner that extends across a width of the liner, the opening including adjacent edges of the first bottom portion and the second bottom portion of the liner.

12. The container according to claim 10, wherein one or both of the first cover and second cover comprises a cover top portion, a cover first bottom portion, a cover second bottom portion, and a cover closure feature, the cover closure feature comprising an opening in the cover that extends across a width of the cover and includes overlapping edges of the cover first bottom portion and the cover second bottom portion.

13. The container according to claim 8, wherein the container is compatibly receivable in a second transportation device, the second transportation device different from the first transportation device, such that the container is exchangeable between the first transportation device and the second transportation device.

14. A method for containing and transporting a medical device using the system of claim 4, comprising:
enclosing the liner about the container, such that the liner conforms to a profile of the container;
receiving a medical device in the inner portion of the container over the liner; and
enclosing the first cover about the container, the liner and the medical device.

15. The system according to claim 1, wherein liner comprises one piece of material forming the top portion and two pieces of material forming the first and second bottom portions.

16. The container of claim 8, wherein the recessed portion of the bottom face extends between two non-recessed portions that extend across an entire width of the bottom face.

* * * * *